United States Patent [19]

Tsuchiya et al.

[11] Patent Number: 6,104,946
[45] Date of Patent: Aug. 15, 2000

[54] MEASURING METHOD AND APPARATUS OF ABSORPTION INFORMATION OF SCATTERING MEDIUM

[75] Inventors: Yutaka Tsuchiya; Yutaka Yamashita, both of Hamamatsu, Japan

[73] Assignee: Technology Research Association of Medical and Welfare Apparatus, Tokyo, Japan

[21] Appl. No.: 08/943,700

[22] Filed: Oct. 3, 1997

[30] Foreign Application Priority Data

Oct. 3, 1996 [JP] Japan ................................ 8-263047

[51] Int. Cl.⁷ .................................................. A61B 6/00
[52] U.S. Cl. ........................ 600/476; 356/432; 356/433
[58] Field of Search ........................... 600/476, 473, 600/478, 475, 310; 356/300, 319, 320, 336, 375, 432, 433

[56] References Cited

U.S. PATENT DOCUMENTS

| | | | |
|---|---|---|---|
| 5,477,051 | 12/1995 | Tsuchiya | 250/341.1 |
| 5,517,987 | 5/1996 | Tsuchiya | 600/310 |
| 5,640,247 | 6/1997 | Tsuchiya et al. | 356/446 |
| 5,676,142 | 10/1997 | Miwa et al. | 600/310 |
| 5,694,931 | 12/1997 | Tsuchiya | 600/310 |
| 5,774,223 | 6/1998 | Urakami et al. | 356/394 |
| 5,899,865 | 5/1999 | Chance | 600/473 |
| 5,936,739 | 8/1999 | Cameron et al. | 356/441 |

FOREIGN PATENT DOCUMENTS

| | | |
|---|---|---|
| 0 280 986 | 9/1988 | European Pat. Off. . |
| 0 710 832 A1 | 5/1996 | European Pat. Off. . |
| 43 30 460 A1 | 3/1995 | Germany . |
| 2 228 314 | 8/1990 | United Kingdom . |

OTHER PUBLICATIONS

Anthony J. Joblin, Method of Calculating the Image Resolution of a Near–Infrared Time–of–Flight Tissue–Imaging System, Applied Optics, Feb. 1996, pp. 752–757.

J. Hebden, D. Hall, M. Firbank and D. Delpy, Time–Resolved Optical Imaging of a Solid Tissue–Equivalent Phantom, Applied Optics, Dec. 1995, pp. 8038–8044.

G. Mitic, J. Kolzer, J. Otto, E. Plies, G. Solkner and W. Zinth, Time–Gated Transillumination of Biological Tissues and Tissuelike Phantoms, Applied Optics, Oct. 1994, pp. 6699–6710.

J. Hebden and D. Delpy, Enhanced Time–Resolved Imaging with a Diffusion Model of Photon Transport, Optics Letters, Mar. 1, 1994, vol. 19, No. 5, pp. 311–313.

J. Moon, R. Mahon, M. duncan and J. Reintjes, Resolution Limits for Imaging Through Turbid Media With Diffuse Light, Optics Letters, Oct. 1, 1993, vol. 18, No. 19, pp. 1591–1593.

A. Cerussi, J. Maier, S. Fantini, M. Franceschini and E. Gratton, The Frequency Domain Multi–Distance Method in teh Presence of Curved Boundaries, Optical Society of America.

*Primary Examiner*—Brian L. Casler
*Attorney, Agent, or Firm*—Pillsbury Madison & Sutro LLP

[57] ABSTRACT

A measuring apparatus of absorption information of scattering medium, comprising a light source for generating pulsed light, a light incidence section for making the pulsed light incident to a scattering medium, a light receiving section for receiving the light having propagated inside the measured object, a signal detecting section for temporally cutting a portion out of a light signal obtained by the light receiving section to acquire a measurement signal corresponding to the cut-out signal, a first arithmetic section for performing a measurement for acquiring measurement signals respectively at plural different timings or the like and for deriving a time integration value and a mean optical pathlength for each of the plural measurement signals obtained, and a second arithmetic section for calculating a change amount of concentration of an absorptive constituent, based on a predetermined relation among plural time integration values, plural mean optical pathlengths, an absorption coefficient per unit concentration of the absorptive constituent, and the change amount of concentration of the absorptive constituent.

22 Claims, 12 Drawing Sheets

ABSORPTION SPECTRA OF
VARIOUS LIVING SUBSTANCES

NEAR-INFRARED ABSORPTION SPECTRA
OF Hb(0.37mM), Mb(0.15mM).

ABSOLUTE SPECTRA

SOLID LINES : OXYGENATED
DOTTED LINES : DEOXYGENATED

CONDENSER LENS

OPTICAL FIBER

PINHOLE

INCIDENCE OF LIGHT FROM INSIDE SCATTERING MEDIUM

DIRECT DETECTION

OPTICAL FIBER

COMBINATION WITH LENS

MEASURING METHOD AND APPARATUS OF ABSORPTION INFORMATION OF SCATTERING MEDIUM

BACKGROUND OF THE INVENTION

1. Field of the Invention

The present invention relates to a measuring method and apparatus capable of obtaining information concerning absorption inside a scattering medium like living tissues and the like, an imaging method and apparatus, a fluoroscopic method and apparatus, a tomographic image taking method and apparatus, or a mammographic method and apparatus. More particularly, the present invention concerns a method and apparatus for measuring a temporal change or a spatial distribution of concentration of a specific absorptive constituent in a specific portion inside a scattering medium and further concerns an absorption information measuring method and apparatus of scattering medium capable of non-invasively measuring a concentration distribution of a specific absorptive constituent inside a scattering medium having surfaces of various shapes.

2. Related Background Art

There are four types of main methods for measuring or imaging a living tissue of a scattering medium by use of light, which are roughly classified into (a) one using translationally propagating light (ballistic photon), (b) one utilizing a coherent component by heterodyne detection thereof, (c) one utilizing scattered light, and (d) one utilizing a time-resolved gate.

(a) The method utilizing the translationally propagating light (ballistic photon) is arranged to make pulsed light incident to a measured object and to extract a translationally transmitted component in output light by an ultra-high-speed gate. On this occasion, a flight time of the translationally transmitted light is shorter than those of scattered light and is shortest among the output light. Therefore, the translationally transmitted light can be detected by cutting out a light part first emerging from the measured object by the ultra-high-speed gate. This method has such an advantage that a high spatial resolution as in X-ray CT can be expected theoretically. However, almost all light is scattered multiply inside the measured object being the scattering medium, and therefore, the translationally transmitted component exists little or, even if present, in a very small amount. As a result, the utilization factor of the light upon measurement becomes very poor and, considering the maximum light incidence intensity (approximately 2 mW/mm$^2$) that can be injected into a living body, an extremely long time becomes necessary for imaging or measurement or the like, which is not practical. With a large object like the head or the arm the signal light is very weak and measurement is impossible in practice.

(b) The method utilizing the coherent component is arranged to split coherent high-frequency modulated light into two components and make one incident to the measured object. Then the output light is made to interfere with the other high-frequency modulated light component to heterodyne-detect the coherent component included in the output light, and the coherent component is used for measurement.

Specifically, since in this measuring system the flight time (or optical pathlength) and the flight direction of scattered light are disordered depending upon the degree of scattering, multiply scattered light does not interfere, and thus nearly translationally transmitted light is detected. Also in this case, therefore, the high spatial resolution is expected theoretically as in the previous example, but the utilization factor of light is very poor, so that it is very difficult to practically apply it to measurement or imaging or the like of living body. It is also practically impossible to measure a large object like the head or the arm.

(c) The method for detecting the scattered light is arranged to make continuous wave (CW) light, pulsed light, or modulated light incident to the measured object and to detect the light (output light) having propagated as scattered in the measured object. On this occasion, where the pulsed light of a sufficiently shorter pulse width than the time response characteristic of the measured object is made incident thereto, it may be considered as incidence of impulse light and the output light corresponding thereto is expressed by an impulse response. The measurement of this type is called as time-resolved spectroscopy (TRS), wherein internal information is calculated by measuring a time-resolved waveform of the impulse response. The method for making the continuous wave (CW) light incident is called as CW spectroscopy and the measurement for making the modulated light incident as phase modulated spectroscopy (PMS). The former measures a time integration value of the impulse response and the latter measures a Fourier transform of the impulse response, i.e., a system function thereof. From the above discussion, it is understood that the time-resolved spectroscopy (TRS) obtains the signal containing more information than the other two methods. The phase modulated spectroscopy (PMS) for sweeping the modulation frequency and the time-resolved spectroscopy (TRS) of impulse response include nearly equivalent information. Since the continuous wave (CW) spectroscopy and the phase modulated spectroscopy (PMS), though greatly different in their signal processing methods, obtain signals including substantially equivalent information, almost equal information can be measured thereby. Since all of these methods utilize almost all output light, their utilization factors of light are increased remarkably as compared with the foregoing two examples of (a) and (b). However, the scattered light spreads in the almost all area or in a considerably wide region inside the measured object, so that the above methods cannot be applied to quantitative measurements in a narrow, specific portion. In imaging or optical CT, the spatial resolution is very poor and practical application is difficult.

In contrast with the above, (d) the method utilizing the time-resolved gate uses a part of the impulse response waveform. For example, photons included in the initial portion of the time-resolved output signal (impulse response waveform) are those little scattered (photons little tarrying on the way), which are photons having propagated near the straight optical path connecting a light incidence position (light incidence point) with a photodetection position (light receiving point). Accordingly, by utilizing the signal from the time-resolved gate, the photons having propagated near the above straight optical path and then detected can be extracted, thus improving the spacial resolution of imaging or the like. The extremity of this is the translationally propagating light (ballistic photon) described previously. The time-resolved gate methods having been developed or proposed heretofore do not permit the quantitative measurements of an absorptive constituent inside the scattering medium. The reason is that no method is developed for analytically describing the signal obtained by the time-resolved gate method. Namely, there are no known methods for analyzing the signal obtained by the time-resolved gate method based on the photon diffusion theory and for utilizing it for quantification of absorptive constituent. Even if a method of analysis based on the photon diffusion theory is developed, there will remain the essential problem resulting from the basis placed on the photon diffusion theory; i.e., there will remain a problem that it is impossible to measure scattering media having various contours and those to which diffusion approximation cannot be applied. From the above, the time-resolved gate method can improve the spatial resolution, but has the serious problem that the internal information of an absorptive constituent or the like cannot be quantified.

There are many references as to the time-resolved gate method as described above and typical examples thereof are listed below. It is, however, noted that none of them presents discussions or suggestions on the quantification of absorptive constituent as disclosed in the present invention.

1) A. J. Joblin, "Method of calculating the image resolution of a near-infrared time-of-flight tissue-imaging system," Appl. Opt. Vol. 35, pp. 752–757 (1996).

2) J. C. Hebden, D. J. Hall, M. Firbank and D. T. Delpy, "Time-resolved optical imaging of a solid tissue-equivalent phantom," Appl. Opt. Vol. 34, pp. 8038–8047 (1995).

3) G. Mitic, J. Kolzer, J. Otto, E. Plies, G. Solkner and W. Zinth, "Time-gated transillumination of biological tissues and tissue-like phantoms," Appl. Opt. Vol. 33, pp. 6699–6710 (1994).

4) J. C. Hebden and D. T. Delpy, "Enhanced time-resolved imaging with a diffusion model of photon transport," Opt. Lett. Vol. 19, pp. 311–313 (1994).

5) J. A. Moon, R. Mahon, M. D. Duncan and J. Reintjes, "Resolution limits for imaging through turbid media with diffuse light," Opt. Lett. Vol. 18, pp. 1591–1593 (1993).

SUMMARY OF THE INVENTION

An object of the present invention is to solve the problem of "incapability of quantitatively measuring the internal information of absorptive constituent or the like," while making full use of the advantage of "capability of achieving the high spatial resolution" of the conventional time gate method described above. Specifically, an object of the present invention is to find out a method (basic relation) for describing the behavior of light inside scattering media of different shapes, to find out a method for applying this basic relation to the time-resolved gate method, and thereby to provide a method and apparatus for measuring a change or an absolute value of concentration of a specific absorptive constituent inside the scattering media of various shapes by use of the foregoing relation without being affected by contours of scattering medium and at high spatial resolution. A further object of the present invention is to provide a measuring method and apparatus of absorption information inside the scattering medium, such as a living-body measuring method and apparatus, an imaging method and apparatus, a fluoroscopic method and apparatus, a tomographic image analyzing method and apparatus, or a mammographic method and apparatus, capable of greatly improving the measurement accuracy as to a specific absorptive constituent in a specific portion and measuring a temporal change or a spatial distribution thereof.

A first measuring method of absorption information of scattering medium according to the present invention is a method comprising:

a first step of generating pulsed light of a predetermined wavelength;

a second step of making said pulsed light incident in a spot shape at a light incidence position in a surface of a scattering medium being a measured object;

a third step of receiving the light having propagated inside the measured object at a photodetection position in the surface of said scattering medium;

a fourth step of temporally cutting a portion out of a light signal obtained in said third step to acquire a measurement signal corresponding to the signal portion thus cut out;

a fifth step of repetitively performing said first to fourth steps at each of plural different timings and deriving a time integration value and a mean optical pathlength for each of plural said measurement signals obtained at said plural timings; and a sixth step of calculating a change amount of absorption coefficient occurring between said plural timings, based on a predetermined relation among plural said time integration values, plural said mean optical pathlengths, and the change amount of absorption coefficient.

In this case, the method may further comprise a seventh step of calculating a change amount of concentration of an absorptive constituent occurring between said plural timings, based on a predetermined relation among the change amount of absorption coefficient obtained in said sixth step, an absorption coefficient per unit concentration of the absorptive constituent, and the change amount of concentration of the absorptive constituent.

In said sixth step, a change amount of concentration of an absorptive constituent occurring between said plural timings may be calculated based on a predetermined relation among said plural time integration values, said plural mean optical pathlengths, an absorption coefficient per unit concentration of the absorptive constituent, and the change amount of concentration of the absorptive constituent.

A second measuring method of absorption information of scattering medium according to the present invention is a method comprising:

a first step of generating pulsed light of a predetermined wavelength;

a second step of making said pulsed light incident in a spot shape at a light incidence position in a surface of a scattering medium being a measured object;

a third step of receiving the light having propagated inside the measured object at a photodetection position in the surface of said scattering medium;

a fourth step of temporally cutting a portion out of a light signal obtained in said third step to acquire a measurement signal corresponding to the signal portion thus cut out;

a fifth step of repetitively performing said first to fourth steps at each of plural different measurement positions while fixing a distance between said light incidence position and said photodetection position, and deriving a time integration value and a mean optical pathlength for each of plural said measurement signals obtained at said plural measurement positions; and a sixth step of calculating a difference of absorption coefficient occurring between said plural measurement positions, based on a predetermined relation among plural said time integration values, plural said mean optical pathlengths, and the difference of absorption coefficient.

In this case, the method may further comprise a seventh step of calculating a difference of concentration of an absorptive constituent occurring between said plural measurement positions, based on a predetermined relation among the difference of absorption coefficient obtained in said sixth step, an absorption coefficient per unit concentration of the absorptive constituent, and the difference of concentration of the absorptive constituent.

In said sixth step, a difference of concentration of an absorptive constituent occurring between said plural measurement positions may be calculated based on a predetermined relation among said plural time integration values, said plural mean optical pathlengths, an absorption coefficient per unit concentration of the absorptive constituent, and the difference of concentration of the absorptive constituent.

A third measuring method of absorption information of scattering medium according to the present invention is a method comprising:

- a first step of generating pulsed light of different wavelengths at which scattering coefficients of a measured object are equal to each other or are regarded as equal to each other;
- a second step of making said pulsed light incident in a spot shape at a light incidence position in a surface of a scattering medium being the measured object;
- a third step of receiving the light having propagated inside the measured object at a photodetection position in the surface of said scattering medium;
- a fourth step of temporally cutting a portion out of a light signal obtained in said third step to acquire a measurement signal corresponding to the signal portion thus cut out so as to keep an identical temporal relation for each of said pulsed light of the different wavelengths;
- a fifth step of obtaining a time integration value and a mean optical pathlength for each of plural said measurement signals; and
- a sixth step of calculating a difference of absorption coefficient for said pulsed light of the different wavelengths, based on a predetermined relation among plural said time integration values, plural said mean optical pathlengths, and the difference of absorption coefficient.

In this case, the method may further comprise a seventh step of calculating a concentration of an absorptive constituent, based on a predetermined relation among the difference of absorption coefficient obtained in said sixth step, absorption coefficients per unit concentration of the absorptive constituent for said pulsed light of the different wavelengths, and the concentration of the absorptive constituent.

In said sixth step, a concentration of an absorptive constituent may be calculated based on a predetermined relation among plural said time integration values, plural said mean optical pathlengths, absorption coefficients per unit concentration of the absorptive constituent for said pulsed light of the different wavelengths, and the concentration of the absorptive constituent.

Further, the method may be arranged more preferably in such a way that in said third step the light is received at a plurality of photodetection positions;

that in said fourth step measurement signals are acquired respectively corresponding to said pulsed light of the different wavelengths at each of said plurality of photodetection positions;

that in said fifth step the temporal integration value and the mean optical pathlength are derived for each of said plural measurement signals; and that in said sixth step said concentration of the absorptive constituent is calculated based on a predetermined relation among plural said time integration values, plural said mean optical pathlengths, absorption coefficients per unit concentration of the absorptive constituent for said pulsed light of the different wavelengths, and the concentration of the absorptive constituent.

Also, the method may further comprise an eighth step of moving the light incidence position in said second step and the photodetection position in said third step along a periphery of the scattering medium being the measured object, calculating the concentration of the absorptive constituent obtained in said sixth step for each of plural measurement positions achieved by said moving, and thereby calculating a tomographic image of concentration distribution in the scattering medium.

A first measuring apparatus of absorption information of scattering medium according to the present invention is an apparatus comprising:

- a light source for generating pulsed light of a predetermined wavelength;
- a light incidence section for making said pulsed light incident in a spot shape at a light incidence position in a surface of a scattering medium being a measured object;
- a light receiving section for receiving the light having propagated inside the measured object at a photodetection position in the surface of said scattering medium;
- a signal detecting section for temporally cutting a portion out of a light signal obtained in said light receiving section to acquire a measurement signal corresponding to the signal portion thus cut out;
- a first arithmetic section for performing a measurement for acquiring said measurement signal at each of plural different timings and deriving a time integration value and a mean optical pathlength for each of plural said measurement signals obtained at said plural timings; and
- a second arithmetic section for calculating a change amount of absorption coefficient occurring between said plural timings, based on a predetermined relation among plural said time integration values, plural said mean optical pathlengths, and the change amount of absorption coefficient.

In this case, said second arithmetic section may further calculate a change amount of concentration of an absorptive constituent occurring between said plural timings, based on a predetermined relation among the change amount of absorption coefficient obtained in said second arithmetic section, an absorption coefficient per unit concentration of the absorptive constituent, and the change amount of concentration of the absorptive constituent.

Also, in said second arithmetic section, a change amount of concentration of an absorptive constituent occurring between said plural timings may be calculated based on a predetermined relation among said plural time integration values, said plural mean optical pathlengths, an absorption coefficient per unit concentration of the absorptive constituent, and the change amount of concentration of the absorptive constituent.

A second measuring apparatus of absorption information of scattering medium according to the present invention is an apparatus comprising:

- a light source for generating pulsed light of a predetermined wavelength;
- a light incidence section for making said pulsed light incident in a spot shape at a light incidence position in a surface of a scattering medium being a measured object;

a light receiving section for receiving the light having propagated inside the measured object at a photodetection position in the surface of said scattering medium;

a signal detecting section for temporally cutting a portion out of a light signal obtained in said light receiving section to acquire a measurement signal corresponding to the signal portion thus cut out;

a first arithmetic section for performing a measurement for acquiring said measurement signal at each of plural different measurement positions while fixing a distance between said light incidence position and said photodetection position, and deriving a time integration value and a mean optical pathlength for each of plural said measurement signals obtained at said plural measurement positions; and a second arithmetic section for calculating a difference of absorption coefficient occurring between said plural measurement positions, based on a predetermined relation among plural said time integration values, plural said mean optical pathlengths, and the difference of absorption coefficient.

In this case, said second arithmetic section may further calculate a difference of concentration of an absorptive constituent occurring between said plural measurement positions, based on a predetermined relation among the difference of absorption coefficient obtained in said second arithmetic section, an absorption coefficient per unit concentration of the absorptive constituent, and the difference of concentration of the absorptive constituent.

Also, in said second arithmetic section, a difference of concentration of an absorptive constituent occurring between said plural measurement positions may be calculated based on a predetermined relation among said plural time integration values, said plural mean optical pathlengths, an absorption coefficient per unit concentration of the absorptive constituent, and the difference of concentration of the absorptive constituent.

A third measuring apparatus of absorption information of scattering medium according to the present invention is an apparatus comprising:

a light source for generating pulsed light of different wavelengths at which scattering coefficients of a measured object are equal to each other or are regarded as equal to each other;

a light incidence section for making said pulsed light incident in a spot shape at a light incidence position in a surface of a scattering medium being the measured object;

a light receiving section for receiving the light having propagated inside the measured object at a photodetection position in the surface of said scattering medium;

a signal detecting section for temporally cutting a portion out of a light signal obtained in said light receiving section to acquire a measurement signal corresponding to the signal portion thus cut out so as to keep an identical temporal relation for each of said pulsed light of the different wavelengths;

a first arithmetic section for obtaining a time integration value and a mean optical pathlength for each of plural said measurement signals; and a second arithmetic section for calculating a difference of absorption coefficient for said pulsed light of the different wavelengths, based on a predetermined relation among plural said time integration values, plural said mean optical pathlengths, and the difference of absorption coefficient.

In this case, said second arithmetic section may further calculate a concentration of an absorptive constituent, based on a predetermined relation among the difference of absorption coefficient obtained in said second arithmetic section, absorption coefficients per unit concentration of the absorptive constituent for said pulsed light of the different wavelengths, and the concentration of the absorptive constituent.

Also, in said second arithmetic section, a concentration of an absorptive constituent may be calculated based on a predetermined relation among plural said time integration values, plural said mean optical pathlengths, absorption coefficients per unit concentration of the absorptive constituent for said pulsed light of the different wavelengths, and the concentration of the absorptive constituent.

Further, the apparatus may be arranged preferably in such a way that said light receiving section receives the light at a plurality of photodetection positions;

that said signal detecting section acquires measurement signals respectively corresponding to said pulsed light of the different wavelengths at each of said plurality of photodetection positions;

that said first arithmetic section derives the time integration value and the mean optical pathlength for each of said plural measurement signals; and that said second arithmetic section calculates said concentration of the absorptive constituent, based on a predetermined relation among plural said time integration values, plural said mean optical pathlengths, absorption coefficients per unit concentration of the absorptive constituent for said pulsed light of the different wavelengths, and the concentration of the absorptive constituent.

Also, the apparatus may further comprise a third arithmetic section for moving the light incidence position in said light incidence section and the photodetection position in said light receiving section along a periphery of the scattering medium being the measured object, calculating the concentration of the absorptive constituent obtained in said second arithmetic section for each of plural measurement positions achieved by said moving, and thereby calculating a tomographic image of concentration distribution in the scattering medium.

The present invention will be more fully understood from the detailed description given hereinbelow and the accompanying drawings, which are given by way of illustration only and are not to be considered as limiting the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will be apparent to those skilled in the art from this detailed description.

DESCRIPTION OF THE PREFERRED EMBODIMENTS (Principle of the Present Invention)

The principle of the present invention will be described first. Herein, the problem in the photon diffusion approximation normally used will be first clarified and then the principle of the present invention will be described.

In general, the behavior of photon inside the scattering medium is analyzed by the photon diffusion equation based on the photon diffusion theory. Namely, the behavior of light inside the scattering medium is approximated by the photon diffusion equation, this equation is solved to obtain a relation between an optical characteristic or an optical constant of the measured object and the output light, and absorption information or the like can be derived from this relation. However, the method based on the photon diffusion equation has the following problem.

Specifically, boundary conditions must be set for solving the photon diffusion equation. However, since the boundary conditions vary greatly depending upon the shape of scattering medium, the photon diffusion equation needs to be solved by setting new boundary conditions for every change of the shape of scattering medium, in order to achieve accurate measurements. However, scattering media for which the boundary conditions can be set accurately to some extent are limited to very simple shapes such as an infinite space, a semi-infinite space, a circular cylinder having the infinite length, a slab spreading infinitely and having a finite thickness, and a sphere. As a result, use of approximate boundary conditions is indispensable in measurements of living tissues having complicated shapes, which is a cause to produce large measuring errors. This problem is also discussed, for example, in the recent literature; Albert Cerussi et al., "The Frequency Domain Multi-Distance Method in the Presence of Curved Boundaries," in Biomedical Optical Spectroscopy and Diagnostics, 1996, Technical Digest (Optical Society of America, Washington D.C., 1996) pp. 24–26. Summarizing the above problem, "any measuring methods that can be systematically applied to scattering media of different shapes have not been developed yet and it is impossible for the conventional technologies to accurately measure the concentration of a specific absorptive constituent inside the scattering media of different shapes systematically."

Therefore, the following discussion first discloses a relation that can be systematically applied to the scattering media of different shapes and then discloses a method for quantifying an absorptive constituent by applying this relation to the time-resolved gate method. In the apparatus and method of the present invention that can quantify internal information of the absorptive constituent or the like at improved spatial resolution, the spatial resolution can be selected by controlling the gate time and timing thereof.

Figure 1:
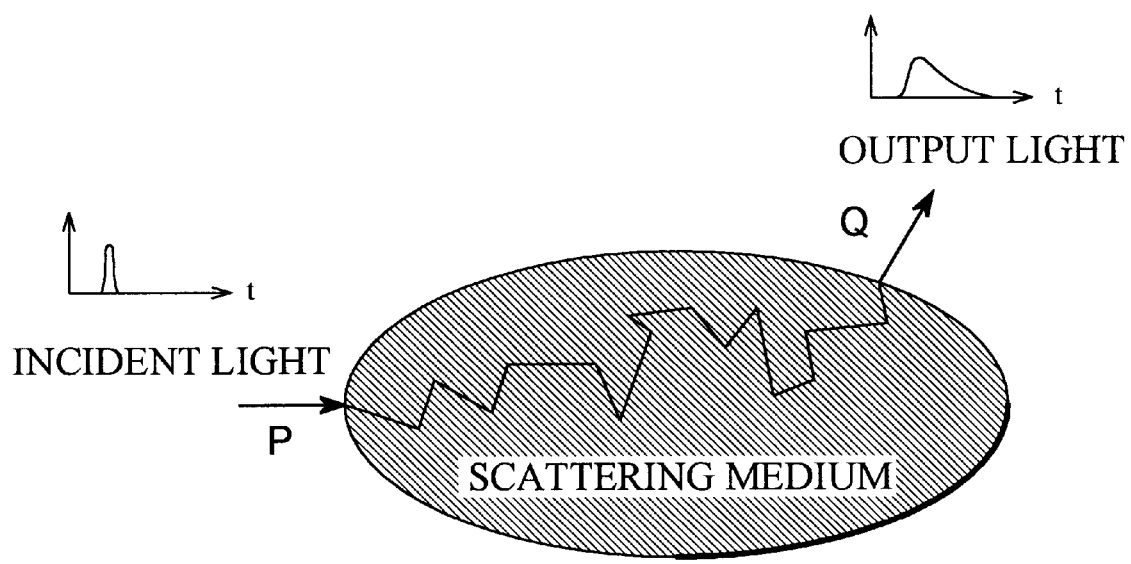
FIG. 1 is a schematic diagram to show the track of the photon having propagated inside the scattering medium.

In non-invasive measurements of the inside of the scattering medium like the living tissues, the light is incident to the surface of the scattering medium, the light having propagated inside the scattering medium is received at another position in the surface to obtain a measurement signal, and information on the concentration or the like of the absorptive constituent contained inside is measured from the measurement signal. On this occasion, photons are strongly scattered by scattering constituents inside the scattering medium and optical paths thereof are bent in a zig-zag pattern. FIG. 1 shows an example of track of a photon where the photon incident at position P is received at position Q. A time-resolved waveform (impulse response) of the output light obtained after incidence of the impulse light to the scattering medium at a reference time t=0 is composed of a plurality of photons having flown in various zig-zag paths and thus having various flight distances (optical pathlengths). However, each of the photons composing the output light at an arbitrary time t has a constant flight distance (optical pathlength) l=ct, where c is the velocity of light in the medium, and the Beer-Lambert law holds for each photon. Namely, the survival rate of each photon is given by $\exp(-c\mu_a t)$ where $\mu_a$ is the absorption coefficient. More specifically, when a light pulse consisting of many photons is incident at position P and received at position Q, many photons having passed through various optical paths are detected at the time t, and the quantity of detected light being the sum thereof, i.e., the survival rate, is proportional to $\exp(-c\mu_a t)$. In the above discussion, the velocity of light c is regarded as constant, because the macroscopic refractive index of living body is a constant value nearly equal to the refractive index of water. The above fact will be called hereinafter as microscopic Beer-Lambert law.

From the above, the impulse response h(t) with incidence of the impulse light to the scattering medium at t=0 becomes a function of scattering coefficient $\mu_s$, absorption coefficient $\mu_a$, and time t, which is expressed as follows.

$$h(t) = s(\mu_s, t)\exp(-\mu_a c t) \tag{1.1}$$

$$\ln h(t) = \ln s(\mu_s, t) - \mu_a c t \tag{1.2}$$

$$\frac{\partial}{\partial \mu_a} \ln h(t) = -ct = -l \tag{1.3}$$

Here, $s(\mu_s, t)$ is a response when the absorption coefficient is $\mu_a=0$ (i.e., a response in the case of only scattering present) and the exponent term $\exp(-\mu_a c t)$ is a term indicating attenuation due to the absorption coefficient $\mu_a$. The all functions are time-causal functions which become zero when t<0. Although the above discussion concerns incidence of impulse light, it is obvious that the above relation also holds for incidence of any pulsed light the time width of which can be regarded as sufficiently shorter than the time response of medium. Accordingly, the following discussion concerns incidence of pulsed light the time width of which can be regarded as sufficiently short.

It should be noted here that the above equations include no variables concerning the boundary conditions. This is a great difference from the solution of the photon diffusion equation including variables concerning the boundary conditions. In the above equations the boundary conditions are reflected through the function $s(\mu_s, t)$ in the impulse response $h(t)$. Therefore, the above equations can be widely applied to scattering media having various non-reentrant surface shapes.

At this time, the output signal $J(\mu_s, \mu_a, t)$ is expressed as follows.

$$J(\mu_s, \mu_a, t) = b\, s(\mu_s, t)\exp(-\mu_a c t) \quad (2.1)$$

$$\ln J(\mu_s, \mu_a, t) = \ln b + \ln s(\mu_s, t) - \mu_a c t \quad (2.2)$$

$$\frac{\partial}{\partial \mu_a} \ln J(\mu_s, \mu_a, t) = -ct = -1 \quad (2.3)$$

Here, b is a coefficient proportional to the intensity of incident light. Time integration of the output signal $J(\mu_s, \mu_a, t)$ indicates total integral output signal quantity $I(\mu_s, \mu_a)$, which corresponds to a measured value in CW spectroscopy. This integral output signal $I(\mu_s, \mu_a)$ is given as follows from Eq. (2.1).

$$I(\mu_s, \mu_a) = b \int_0^\infty s(\mu_s, t)\exp(-\mu_a c t)dt \quad (3.1)$$

$$\frac{\partial}{\partial \mu_a} I(\mu_s, \mu_a) = -bc \int_0^\infty t s(\mu_s, t)\exp(-\mu_a c t)dt \quad (3.2)$$

Figure 2:
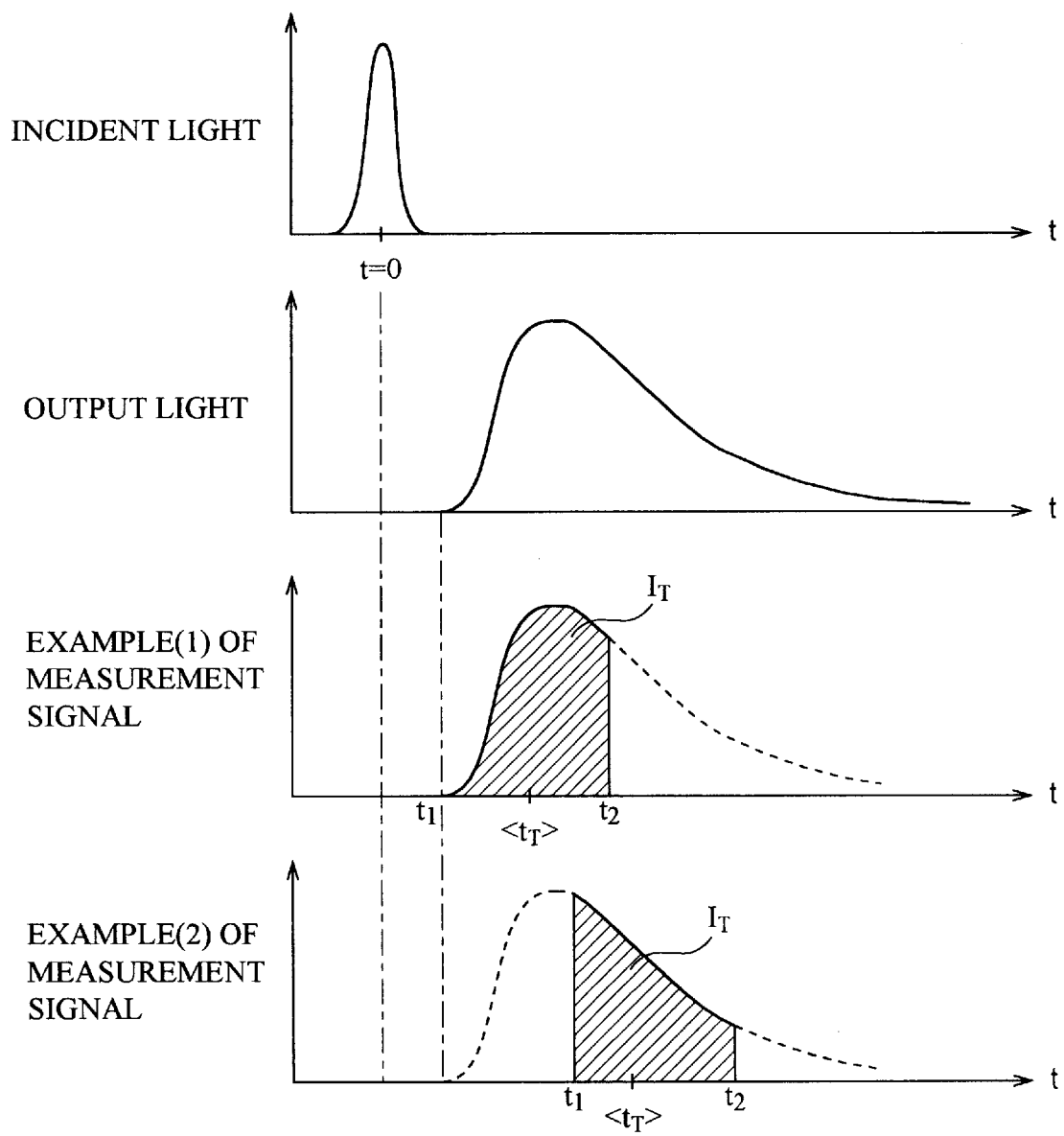
FIG. 2 is waveform diagrams for explaining measurement signals (cut-out signals) according to the present invention.

Now, let us consider that an arbitrary portion $t=[t_1, t_2]$ ($t_1 < t_2$) is cut out of the output signal $J(\mu_s, \mu_a, t)$, as shown in FIG. 2. The integral output signal, i.e., measurement signal $I_T(\mu_s, \mu_a)$ at this time, is expressed by the following equation.

$$I_T(\mu_s, \mu_a) = b \int_{t_1}^{t_2} s(\mu_s, t)\exp(-\mu_a c t)dt \quad (4.1)$$

$$\frac{\partial}{\partial \mu_a} I_T(\mu_s, \mu_a) = -bc \int_{t_1}^{t_2} t s(\mu_s, t)\exp(-\mu_a c t)dt \quad (4.2)$$

Further, the following is derived from Eqs. (4.1) and (4.2).

$$\frac{\partial}{\partial \mu_a} \ln I_T(\mu_s, \mu_a) = \frac{1}{I_T(\mu_s, \mu_a)} \frac{\partial}{\partial \mu_a} I_T(\mu_s, \mu_a) \quad (5)$$

$$= -\frac{c \int_{t_1}^{t_2} t s(\mu_s, t)\exp(-\mu_a c t)dt}{\int_{t_1}^{t_2} s(\mu_s, t)\exp(-\mu_a c t)dt}$$

$$= -c \langle t_T \rangle$$

$$= -L_T(\mu_s, \mu_a)$$

Here, $\langle t_T \rangle$ is a mean flight time of photons detected and $L_T(\mu_s, \mu_a)$ is a mean optical pathlength thereof. This idea is first disclosed by the present invention. Next, integrating Eq. (5), the following is attained.

$$\ln I_T(\mu_s, \mu_a) = -\int_0^{\mu_a} L_T(\mu_s, \mu_a)d\mu_a + \ln \int_{t_1}^{t_2} s(\mu_s, t)dt + \ln b \quad (6)$$

Here, the second and third terms in the right side are integration constants, which are obtained by setting $\mu_a=0$ in Eq. (4.1). Equation (6) includes no variables concerning the boundary conditions, though it is a naturally expected result. This is greatly different from the solution of the photon diffusion equation always including the variables concerning the boundary conditions. In aforementioned Eq. (6), the boundary conditions are reflected in the measurement signal $I_T(\mu_s, \mu_a)$ and mean optical pathlength $L_T(\mu_s, \mu_a)$. Accordingly, Eq. (6) can be widely applied to the scattering media having various non-reentrant surface shapes.

Figure 3A:
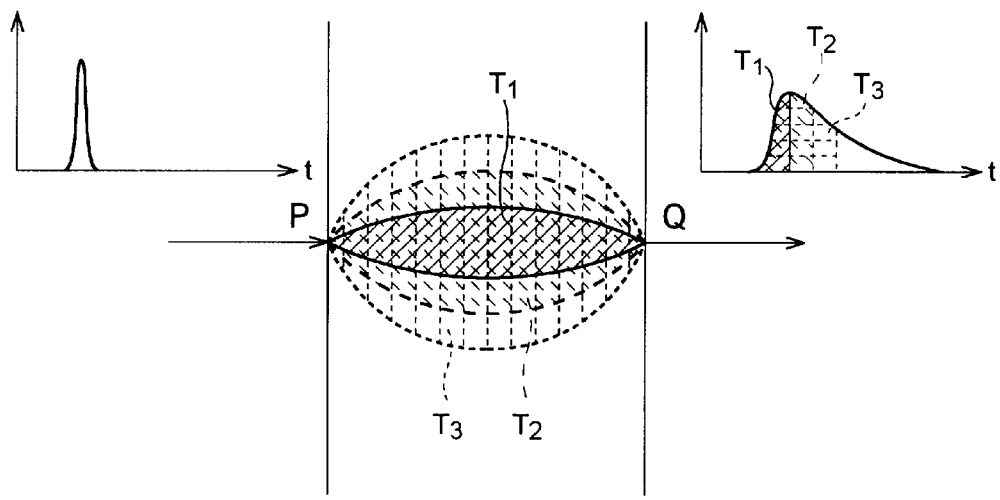
FIGS. 3A and 3B are schematic diagrams, each showing a relation between the cut-out time and the measuring portion (a portion inside the scattering medium).
Figure 3B:
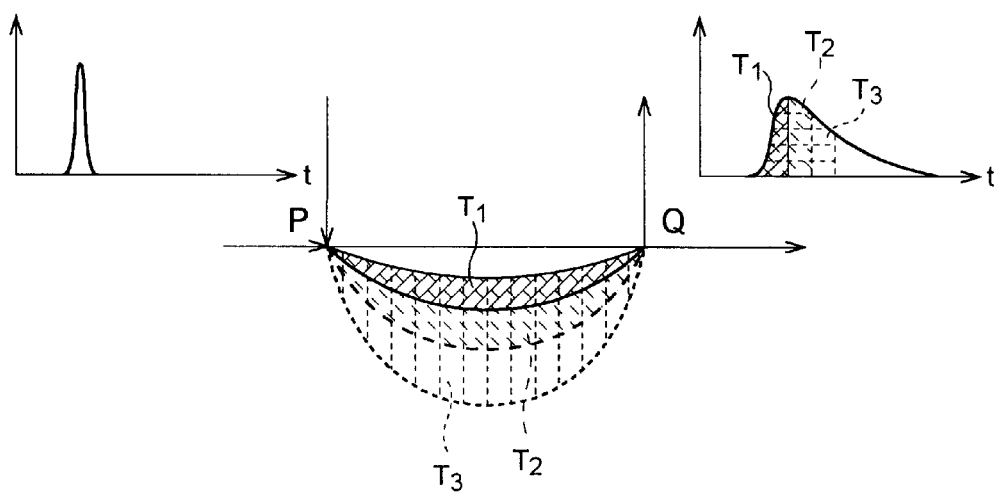

Here, the following can be understood by considering tracks of photons composing the measurement signal obtained by cutting a portion out of the output signal $J(\mu_s, \mu_a, t)$. When only the initial part is cut out of the output signal $J(\mu_s, \mu_a, t)$, photons of short optical pathlengths are detected as described previously, and thus, the detected photons are those having propagated in the narrow portion indicated by solid-line hatching ($T_1$) in FIG. 3A and FIG. 3B, which improves the spatial resolution. FIG. 3A shows an arrangement of transmission type measurement while FIG. 3B an arrangement of reflection type measurement. As the cut-out time $T=t_2-t_1$ increases ($T_1 \rightarrow T_2 \rightarrow T_3$), photons having propagated in successively increasing areas come to be detected as shown by dotted-oblique-line hatching ($T_2$) and dotted-vertical-line hatching ($T_3$) in FIG. 3A and FIG. 3B, whereby the quantity of light (or quantity of signal) utilized in measurement increases, but the spatial resolution is lowered.

Figure 4A:
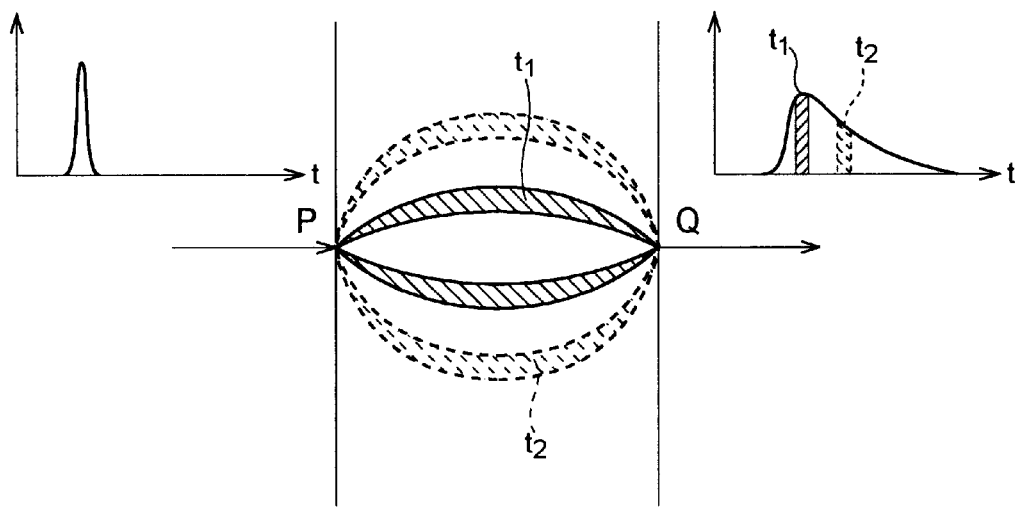
FIGS. 4A and 4B are schematic diagrams, each showing the relation between the cut-out timing and the measuring portion (a portion inside the scattering medium).
Figure 4B:
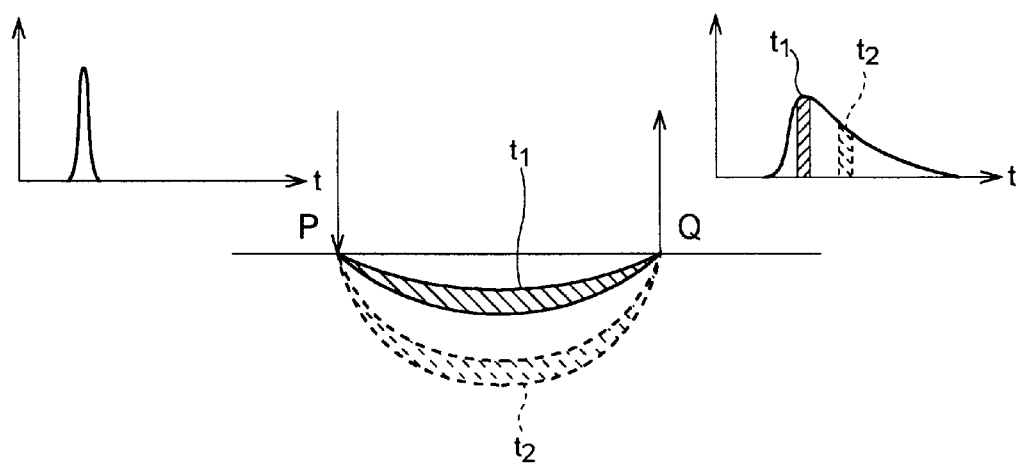

Further, in the case of an intermediate portion being cut out of the output signal $J(\mu_s, \mu_a, t)$, as the cut-out timing becomes later, the measured portion can be changed as shown in FIG. 4A and FIG. 4B ($t_1 \rightarrow t_2$). The measurement of this type can also be realized in measurements for obtaining a difference between two signals obtained by different time gates. Namely, it is utilized that when a later part is cut out of the output signal $J(\mu_s, \mu_a, t)$, it includes more information about the peripheral portion. Therefore, in the present invention, the spatial resolution and the information-acquiring portion can be selected by controlling the foregoing cut-out time $T=t_2-t_1$ and cut-out timing.

It is noted that FIG. 3A, FIG. 3B, FIG. 4A and FIG. 4B show ranges of tracks of ordinary photons forming a certain proportion of photons included in the detected light (output signal). Accordingly, the detected photons also include those having propagated outside the illustrated ranges, of course.

The following will describe methods for calculating information concerning absorption from measured values by use of foregoing Eq. (6).

(Measurement of concentration change of absorptive constituent)

Let us consider a case wherein the medium contains one type of absorptive constituent and the concentration thereof has changed so as to cause the absorption coefficient $\mu_a$ to change from $\mu_{a1}$ to $\mu_{a2}$. With ordinary living bodies and scattering media, the scattering characteristics can be considered not to change with change in the concentration of absorptive constituent. This is just as if ink is put in milk. When $s(\mu_s, t)$ or scattering coefficient $\mu_s$ is invariant before and after the change, the mean optical pathlength $L_T(\mu_s, \mu_a)$ is given by a function of absorption coefficient $\mu_a$ by performing measurements while fixing the measuring position (the pulsed light incident position and photodetection position), and Eq. (6) holds for measured values before and after the change. Accordingly, the following equation is derived from Eq. (6), using $\mu_{a1}$ and $\mu_{a2}$ before and after the change.

$$\ln \frac{I_T(\mu_s, \mu_{a1})}{I_T(\mu_s, \mu_{a2})} = \int_{\mu_{a1}}^{\mu_{a2}} L_T(\mu_s, \mu_a) d\mu_a \quad (7)$$

Then applying the mean value theorem, the following equation is attained from Eq. (7).

$$\ln \frac{I_T(\mu_s, \mu_{a1})}{I_T(\mu_s, \mu_{a2})} = (\mu_{a2} - \mu_{a1})L_T(\mu_s, \mu_x) \quad (8)$$

However, $\mu_x$ is a suitable value satisfying $\mu_{a1} \leq \mu_x \leq \mu_{a2}$ or $\mu_{a1} \geq \mu_x \geq \mu_{a2}$. The above tells us that once the mean optical pathlength $L_T(\mu_s, \mu_x)$ is known, the difference between the absorption coefficients before and after the change, $\mu_{a2}-\mu_{a1}$, can be calculated from the values of measurement signal $I_T(\mu_s, \mu_a)$ before and after the change.

In this case, the mean optical pathlength $L_T(\mu_s, \mu_x)$ can be further expressed as follows using coefficient $\alpha$.

$$L_T(\mu_s,\mu_x)=\alpha L_T(\mu_s,\mu_{a1})+(1-\alpha)L_T(\mu_s,\mu_{a2}) \quad (9)$$

However, $\alpha$ is a suitable value satisfying $0 \leq \alpha \leq 1$. In this case, $L_T(\mu_s, \mu_x)$ is a monotonic function and, because values thereof at $\mu_{a1}$ and at $\mu_{a2}$ are normally nearly equal to each other, $\alpha=\frac{1}{2}$ may be assumed. The mean optical pathlengths $L_T(\mu_s, \mu_{a1})$ and $L_T(\mu_s, \mu_{a2})$ of the respective cases can be obtained by calculating the barycenter of waveform of measurement signal (mean time delay), as indicated in foregoing Eq. (5). Namely, values are calculated of the equation in the second line of aforementioned Eq. (5). Here, since c is the velocity of light in the medium, it can be known by a well-known method or another method. The term included in the numerator and the denominator, which is $s(\mu_s, t)\exp(-\mu_a ct)=A$, is the output signal $J(\mu_s, \mu_a, t)$ in foregoing Eq. (2.1) multiplied by 1/b. This coefficient b can be swept out of the integration and, because both the numerator and denominator include the coefficient, it is eliminated. This means that the above calculation obtains the same result by use of either A or the measured value $J(\mu_s,\mu_a, t)$ of bA. Therefore, the numerator is an integration of $J(\mu_s, \mu_a, t)$ and the denominator an integration of $J(\mu_s, \mu_a, t)$ over t each from $t_1$ to $t_2$. Calculation of these two terms and the ratio thereof can be done at high speed using a computer. Also, the above calculation of barycenter can be made not only by the method for directly calculating the numerator and the denominator in the second line of Eq. (5) as described above, but also by one of various methods equivalent thereto. In either case, the result of this calculation gives the mean flight time and it is multiplied by aforementioned c to obtain the mean optical pathlength.

For calculating concentration change $\Delta V$ of an absorptive constituent, the following equation derived from the Beer-Lambert law is used.

$$\epsilon \Delta V = \mu_{a2} - \mu_{a1} \quad (10)$$

Here, $\epsilon$ is an absorption coefficient (or extinction coefficient) per unit concentration of the absorptive constituent, which can be measured by a spectrophotometer. Absorption coefficients (or extinction coefficients) of many absorptive substances are published in various literature. Therefore, the following is obtained from Eqs. (8) to (10).

$$\Delta V = \frac{1}{\epsilon L_T(\mu_s, \mu_x)} \ln \frac{I_T(\mu_s, \mu_{a1})}{I_T(\mu_s, \mu_{a2})} \quad (11)$$

Equation (11) above clearly shows the method for measuring the concentration change $\Delta V$ of absorptive constituent in the scattering medium.

(Application of measurement of concentration change of absorptive constituent)

The above method can be applied to measurements of temporal changes of concentrations of plural absorptive constituents by using pulsed light of different wavelengths while fixing the measuring position. Further, the method can also be applied to measurements of temporal change in the concentration of hemoglobin in a predetermined portion, by repeating measurements at plural positions along a periphery of a measured object and performing a tomogram reconstruction arithmetic as in X-ray CT, optical CT, or the like.

It is also possible to measure a distribution of difference from a reference value of concentration of an absorptive constituent inside a scattering medium, by performing the measurements while translationally moving or scanning the measuring position (the light incidence position and photodetection position) relative to the measured object held so as to keep its thickness constant, and using a measured value at an arbitrary position, as a reference value. The measurement of this type can be applied to photo-mammography for carrying out diagnosis of breast cancer.

In the above measurements according to the present invention, the spatial resolution is enhanced by shortening the gate time (cut-out time). It is also possible to control a region (or a portion) to be measured, by making the timing of gate variable. Specific application examples include a fluoroscope, optical CT, a clinical monitor utilized in surgery or cure, and so on, in addition to the photo-mammography.

(Measurement of concentration of specific absorptive constituent)

Next described is a measurement using two pulsed light beams of wavelengths $\lambda_1$ and $\lambda_2$, i.e., the dual-wavelength spectrophotometry. Now, let us suppose that the absorption coefficient of the scattering medium containing one absorptive constituent is $\mu_{a1}$ at wavelength $\lambda_1$ and $\mu_{a2}$ at wavelength $\lambda_2$. It is also assumed that the scattering coefficients $\mu_{s1}$ and $\mu_{s2}$ of the medium at the wavelengths $\lambda_1$ and $\lambda_2$ are equal to each other or nearly equal to each other. Such conditions are realized readily by selecting the wavelengths used for measurement. Accordingly, in the case of the dual-wavelength spectroscopy at the fixed measuring position (the pulsed light incidence position and photodetection position), the following relations hold assuming $\mu_{s1} \approx \mu_{s2} = \mu_s$.

$$s(\mu_{s1},\mu_a) \approx s(\mu_{s2},\mu_a) \equiv s(\mu_s,\mu_a) \quad (12.1)$$

$$L_T(\mu_{s1},\mu_a) \approx L_T(\mu_{s2},\mu_a) \equiv L_T(\mu_s,\mu_a) \quad (12.2)$$

Then the following is attained from Eq. (6).

$$\ln \frac{I_T(\mu_s, \mu_{a1})}{I_T(\mu_s, \mu_{a2})} = \ln \frac{I_T(\lambda_1)}{I_T(\lambda_2)} \quad (13)$$

$$\approx \int_{\mu_{a1}}^{\mu_{a2}} L_T(\mu_s, \mu_a) d\mu_a + \ln \frac{b_1}{b_2}$$

Then the following equation is obtained in the same manner as in the case of Eq. (8).

$$\ln \frac{I_T(\lambda_1)}{I_T(\lambda_2)} = (\mu_{a2} - \mu_{a1})L_T(\mu_s, \mu_x) + \ln \frac{b_1}{b_2} \quad (14)$$

However, $\mu_x$ is a suitable value satisfying $\mu_{a1} \leq \mu_x \leq \mu_{a2}$ or $\mu_{a1} \geq \mu_x \geq \mu_{a2}$. When $b_1/b_2=1$, that is, when incident light intensities of the pulsed light beams of two wavelengths are equal to each other, this Eq. (14) becomes equal to aforementioned Eq. (7). The coefficient $b_1/b_2$ can be set to $b_1/b_2=1$ by adjusting the intensities of incident pulsed light beams. Further, it is also possible to estimate the value of $b_1/b_2$ by actually measuring intensities of light sources or pulsed light beams. Based on the above, the difference between the absorption coefficients, $\mu_{a2}-\mu_{a1}$, can be calculated from the values of mean optical pathlength $L_T(\mu_s, \mu_x)$ and $b_1/b_2$, and the values of measurement signals $I_T(\lambda_1)$ and $I_T(\lambda_2)$ obtained in the measurement using the pulsed light beams of the wavelengths $\lambda_1$ and $\lambda_2$.

The mean optical pathlength $L_T(\mu_s, \mu_x)$ can be expressed as follows using the same coefficient $\alpha$ as described above.

$$L_T(\mu_s, \mu_x) = \alpha L_T(\mu_s, \mu_{a1}) + (1-\alpha)L_T(\mu_s, \mu_{a2}) \quad (15)$$

However, $\alpha$ is a suitable value satisfying $0 \leq \alpha \leq 1$. Also in this case, considering the fact that $L_T$ is the monotonic function, $\alpha = \frac{1}{2}$ may be assumed normally. Each of the mean optical pathlengths $L_T(\mu_s, \mu_{a1})$ and $L_T(\mu_s, \mu_{a2})$ can be obtained by calculating the barycenter of the waveform of measurement signal (mean time delay) as shown in foregoing Eq. (5).

The concentration V of the specific absorptive constituent is calculated from the following equation, using the absorption coefficients (or extinction coefficients) $\epsilon_1$ and $\epsilon_2$ per unit concentration of the specific absorptive constituent at the wavelengths $\lambda_1$ and $\lambda_2$.

$$V(\epsilon_2 - \epsilon_1) = \mu_{a2} - \mu_{a1} \quad (16)$$

Here, the values of $\epsilon_1$ and $\epsilon_2$ can be preliminarily measured by the spectrometer. Accordingly, the following equation is obtained.

$$V = \frac{1}{(\epsilon_2 - \epsilon_1)L_T(\mu_s, \mu_x)} \ln \frac{b_2 I_T(\lambda_1)}{b_1 I_T(\lambda_2)} \quad (17)$$

Thus, the absolute concentration V of absorptive constituent can be measured in the same manner as the measurement of concentration change of absorptive constituent described previously. In this case, concentrations of (n−1) types of absorptive constituents can be measured using pulsed light beams of n wavelengths of two or more kinds.

(Two-point dual-wavelength measurement)

When the above-stated dual-wavelength spectrophotometry is carried out at two detection distances (distances between the light incidence and photodetection positions), the aforementioned coefficient $b_1/b_2$ can be eliminated. Namely, the coefficient $b_1/b_2$ is eliminated by utilizing no dependence of the coefficient $b_1/b_2$ on the light incidence and photodetection positions. In this case, aforementioned Eq. (17) becomes as follows.

$$V = \frac{1}{(\epsilon_2 - \epsilon_1)[L_{T1}(\mu_s, \mu_{x1}) - L_{T2}(\mu_s, \mu_{x2})]} \times \ln \frac{I_{T1}(\lambda_1)I_{T2}(\lambda_2)}{I_{T1}(\lambda_2)I_{T2}(\lambda_1)} \quad (18)$$

Here, $I_{T1}(\lambda_1)$, $I_{T2}(\lambda_2)$ and $L_{T1}(\mu_s, \mu_{x1})$, $L_{T2}(\mu_s, \mu_{x2})$ are measurement signals and mean optical pathlengths obtained at photodetection distances 1 and 2, respectively. Further, $\mu_{x1}$ is a suitable value satisfying $\mu_{a1} \leq \mu_{x1} \leq \mu_{a2}$ or $\mu_{a1} \geq \mu_{x1} \geq \mu_{a2}$ and $\mu_{x2}$ is a suitable value satisfying $\mu_{a1} \leq \mu_{x2} \leq \mu_{a2}$ or $\mu_{a1} \geq \mu_{x2} \geq \mu_{a2}$, each of which can be obtained in the same manner as in Eq. (15). Further, it is a matter of course that the above-stated method can be expanded to multi-wavelength spectrophotometry using light beams of two or more wavelengths.

(Measurement of spatial distribution of concentration of absorptive constituent)

A spatial distribution of concentration of absorptive constituent can be measured by performing the above-stated measurement at multiple points. In this case, the detection distance (the distance between the light incidence and photodetection positions) at each measuring point may differ, because a measured value of concentration of absorptive constituent is measured independently of other values. Namely, the method of the present invention can measure concentrations of the absorptive constituent inside the scattering media having various non-reentrant contours at high spatial resolution. On this occasion, the spatial resolution is controlled by the aforementioned cut-out time $T=t_2-t_1$ and the timing thereof. Specific application examples include the photo-mammography, fluoroscope, optical CT, and so on. These applications make use of methods of light reception at plural points, scanning of light incidence position and photodetection position, time-sharing measurement, and so on. The image reconstruction arithmetic as in CT is carried out as occasion may demand. The feature of these measurements is the capability of quantitatively measuring the concentration distribution of specific absorptive constituent at high spatial resolution, as described above.

EMBODIMENTS

Embodiments of the present invention will be described with reference to the accompanying drawings. It is, however, noted that in the following description the same elements will be denoted by the same reference symbols and redundant description will be omitted.

Embodiment 1

Figure 5:
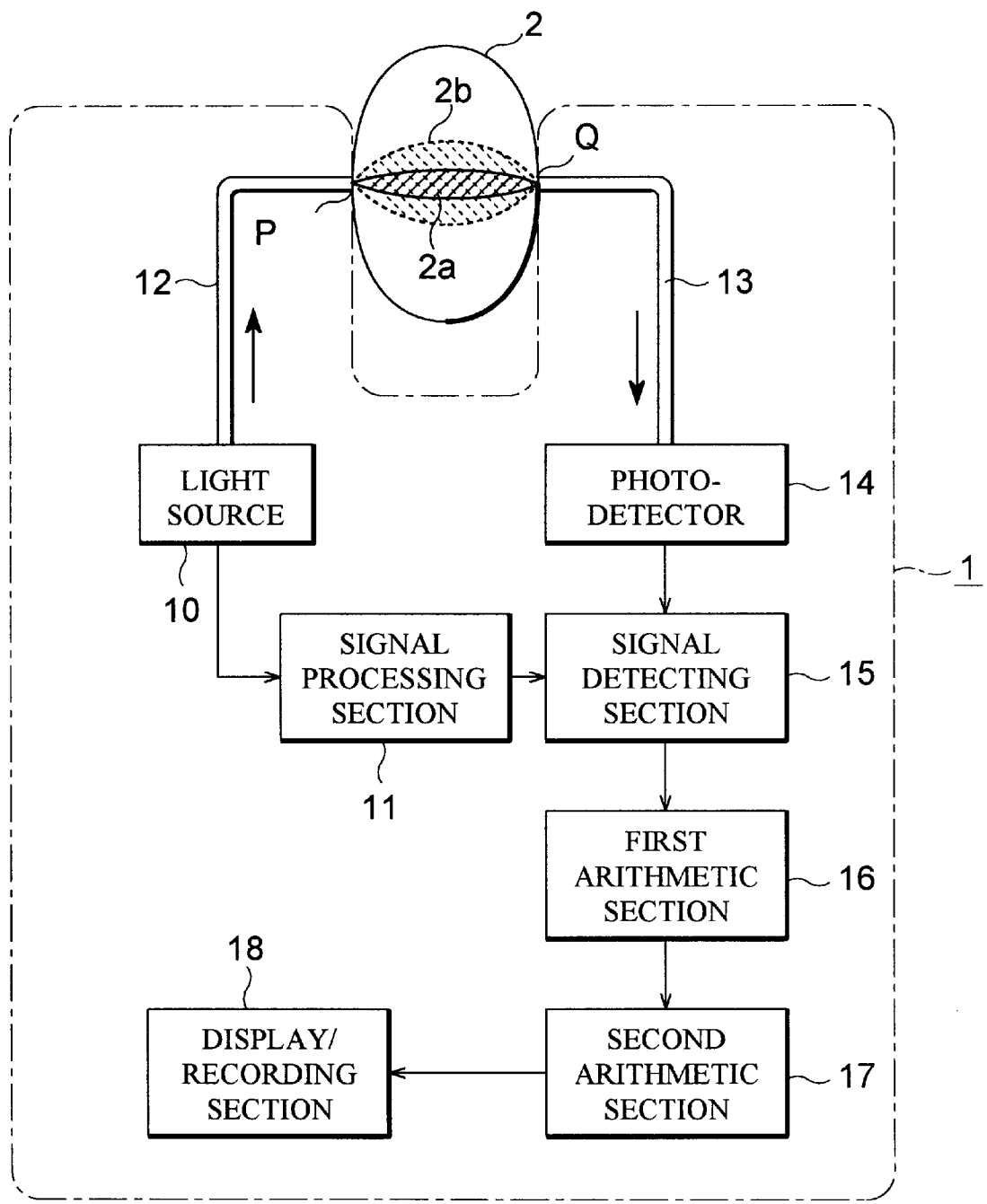
FIG. 5 is a schematic diagram to show the configuration of the apparatus in the first embodiment according to the present invention.

FIG. 5 shows the first embodiment of the apparatus of the present invention for carrying out the method of the present invention and illustrates the configuration of apparatus 1 for measuring a temporal change of concentration of an absorptive constituent inside the scattering medium 2. This configuration of apparatus 1 is arranged to measure a concentration change of an absorptive constituent in scattering medium 2 containing one type of absorptive constituent or to measure a concentration change of an absorptive substance comprised of a plurality of constituents. In this configuration, pulsed light of a sufficiently narrow time width and of predetermined wavelength X is made incident at position P (light incidence position) in the surface of scattering medium 2 and the light having propagated inside the scattering medium 2 is received at another position Q (photodetection position) in the surface. Then this measurement is repeated to quantify a change of concentration of the absorptive constituent in a relatively narrow portion inside the scattering medium 2. In this case, the change of concentration of the absorptive constituent can be quantified by using a concentration of the absorptive constituent obtained in the first measurement, as a reference value. The measuring apparatus 1 is integrally housed in one casing.

Figure 6:
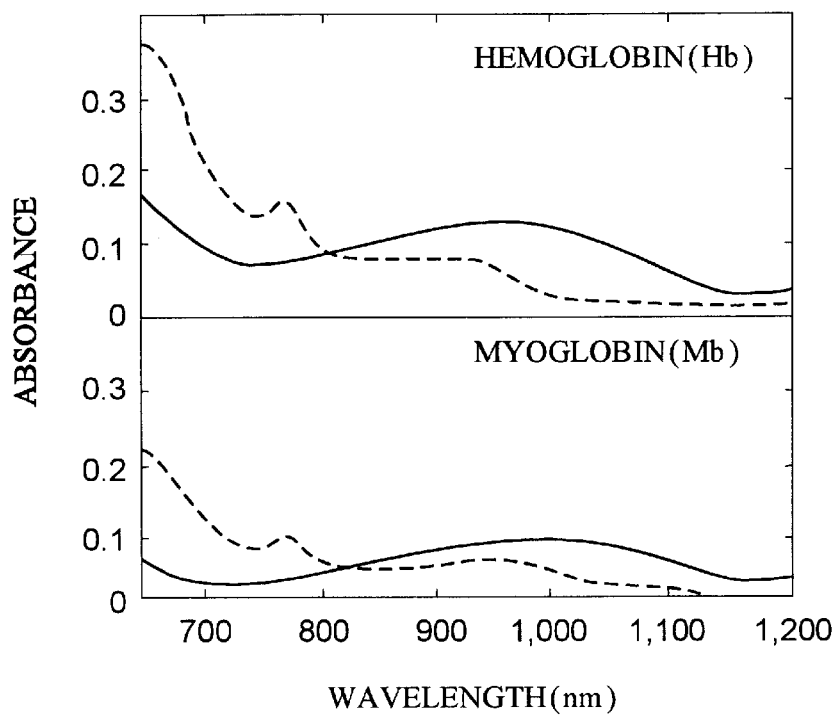
FIG. 6 is a graph to show the absorption spectra of hemoglobin and myoglobin.

Light source 10 is a laser diode or the like and generates the pulsed light of wavelength A. In this case, the wavelength is selected depending upon the scattering medium 2 or the absorptive constituent to be measured. In measurements of living bodies, oxygenated and deoxygenated hemoglobin and oxygenated and deoxygenated myoglobin is often measured and absorption spectra of those absorptive constituents are shown in FIG. 6. Therefore, the light of 600 nm to 1.3 μm is normally used for the measurements of living bodies. The pulse width is normally approximately 20 ps to 200 ps. The light source may be a light-emitting diode, a pulse laser, or the like, as well as the laser diode.

The pulsed light emitted from the light source 10 is made incident through light guide 12 to the surface of scattering medium 2 being a measured object. The space between the light guide 12 and the scattering medium 2 is very small in the embodiment of FIG. 5. However, in practice, this space may be expanded and may be filled with a liquid substance or a jelly substance (hereinafter referred to as an interface material) having the refractive index and scattering coefficient nearly equal to those of the scattering medium 2. Namely, no problem arises, because the light propagates in this interface material to enter the measured object. In the case wherein reflection on the surface of scattering medium 2 is problematic, influence of the surface reflection or the like can be decreased by properly selecting the interface material.

The light having propagated inside the scattering medium 2 is received by light guide 13 placed at position Q (photodetection position) the distance r apart from the aforementioned light incidence position P. The interface material may also be used herein for the same reason as above. Photodetector 14 converts the light signal to an electric signal, amplifies it if necessary, and outputs it. The photodetector 14 may be selected from a phototube, a photodiode, an avalanche photodiode, a PIN photodiode, a streak camera, a streak scope, a photo-oscilloscope, and so on, as well as a photomultiplier tube. In selection of the photodetector 14, it is expected to have the spectral sensitivity characteristics for detecting the light of predetermined wavelengths and the necessary temporal response speed. For weak light signals, a high-gain photodetector is used. Further, the time correlation photon counting method for counting photons may be applied. The places other than the light receiving surface of the photodetector are desirably constructed in structure for absorbing or intercepting the light.

Signal detecting section 15 cuts a predetermined time zone out of the detection signal to output a measurement signal. Specifically, a gate circuit well known is utilized. On this occasion, a gate signal for cutting out the predetermined time zone is generated in signal processing section 11. In this case, the signal processing section 11 uses a signal synchronized with the pulsed light generated from the light source 10 as occasion may demand. The time resolution can be controlled by making the time width (gate time) of the gate signal variable. It is also possible to select a portion to be measured by changing the timing of gate signal. For example, when a fore portion of the detection signal is extracted by a narrow gate, the light having propagated through a narrow portion 2a inside the scattering medium is measured, while the light having propagated through a wider portion 2b than the portion 2a is measured with increasing gate time. Further, it is also possible to employ the controls as shown in foregoing FIGS. 3A and 3B and FIGS. 4A and 4B.

Figure 7:
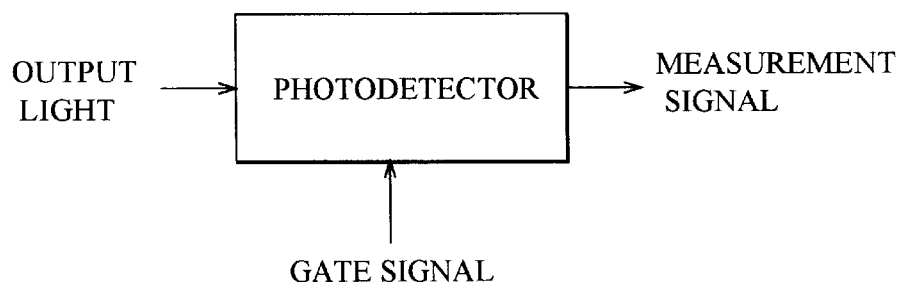
FIG. 7 is a schematic diagram to show another method for obtaining the measurement signal.
Figure 8:
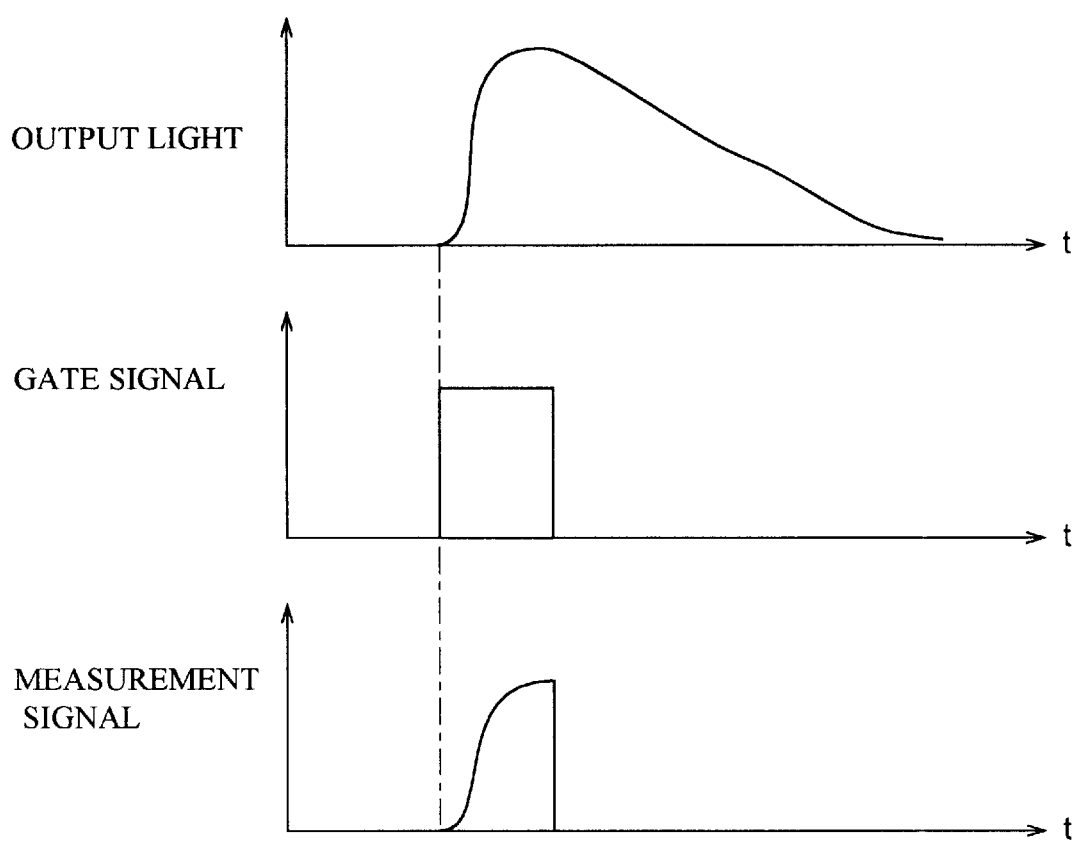
FIG. 8 is waveform diagrams to show the relation among the output light, the gate signal, and the measurement signal in the case of the method shown in FIG. 7.

The above acquisition of measurement signal may be made by another method, for example, by direct gating by the photodetector, as shown in FIG. 7 and FIG. 8. For example, in the case of use of a photomultiplier tube, the gate operation can be made by applying a pulsed voltage to the photocathode, to the first dynode or another dynode, or to the cathode. With an avalanche photodiode, it is also possible to effect the gate operation by applying the pulsed voltage thereto. The streak camera also has the time gate function. In these cases, one device can carry out the photoelectric conversion and gate operation.

First arithmetic section 16 calculates the time integration value $I_T$ and mean optical pathlength $L_T$ (corresponding to the barycenter of waveform (mean delay time)) from the measurement signal. On this occasion, the mean optical pathlength $L_T$ is calculated according to aforementioned Eq. (5). Then the above measurement is repetitively carried out at different times. In the following discussion we consider the m-th and (m+1)-th measurements.

Second arithmetic section 17 substitutes the two types of aforementioned time integration values $I_{T, m}$ and $I_{T, m+1}$ obtained in the m-th and (m+1)-th measurements and the mean optical pathlength $L_T(\mu_s, \mu_x)$ obtained from the two types of aforementioned mean optical pathlengths $L_{T, m}$ and $L_{t, m+1}$ by use of Eq. (9), into aforementioned Eq. (8) to calculate a change amount between the absorption coefficients of the portion of scattering medium 2, $\mu_{a(m+1)} - \mu_{am}$ (primary information), and further calculates a change amount of the absorptive constituent (secondary information) by use of aforementioned Eq. (11). At this time, sufficient accuracy is assured with $\alpha = \frac{1}{2}$ in aforementioned Eq. (8) for calculation of the mean optical pathlength $L_T(\mu_s, \mu_x)$. These arithmetic processes are carried out at high speed by microcomputers or the like incorporated in the first and second arithmetic sections.

Display/recording section 18 has a function to store the concentration information of absorptive constituent obtained as described above, and displays or records these.

The above description concerned use of the pulsed light of one wavelength, but in practice pulsed light of two or more wavelengths can also be applied. Further, it is also possible to make the pulsed light incident at one light incidence position and to detect the propagating light at two or more photodetection positions. These may be detected in parallel or in time division.

Figure 9A:
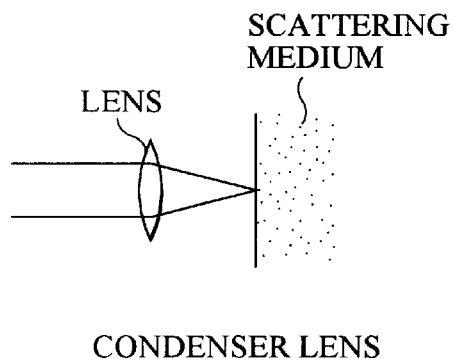
FIGS. 9A, 9B, 9C and 9D are schematic diagrams, each showing a light incidence method to the scattering medium.
Figure 9B:
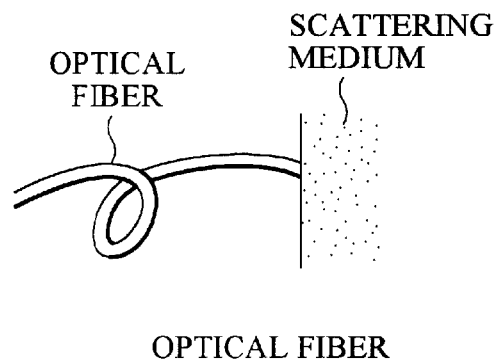
Figure 9C:
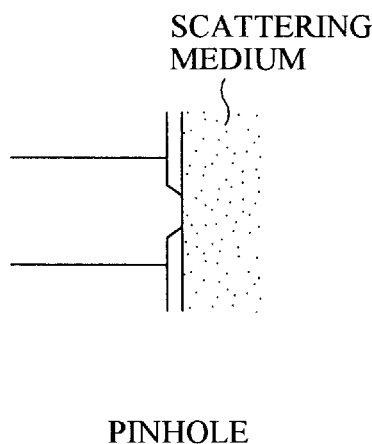
Figure 9D:
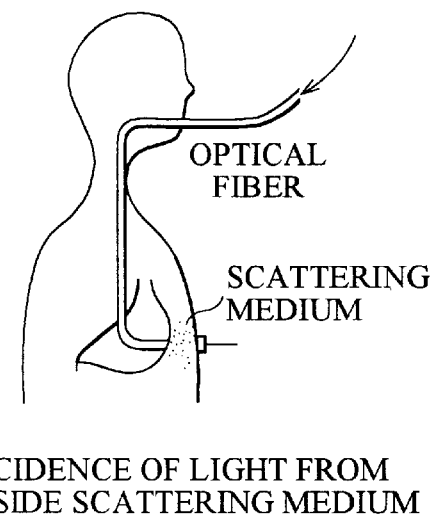

The means for making the light incident to the scattering medium 2 may be selected instead of the light guide 12 shown in FIG. 5 from a method with a condenser lens (FIG. 9A), a method using an optical fiber (FIG. 9B), a method utilizing a pinhole (FIG. 9C), a method for making the light incident from inside a body like a gastrocamera (FIG. 9D), and so on. A thick beam of light may be made incident to the scattering medium. This case may be considered as an arrangement of plural spot light sources being arrayed.

Figure 10A:
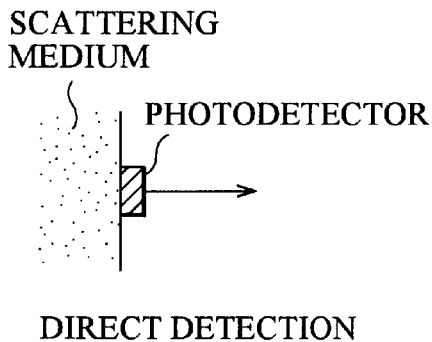
FIGS. 10A, 10B and 10C are schematic diagrams, each showing a light receiving method.
Figure 10B:
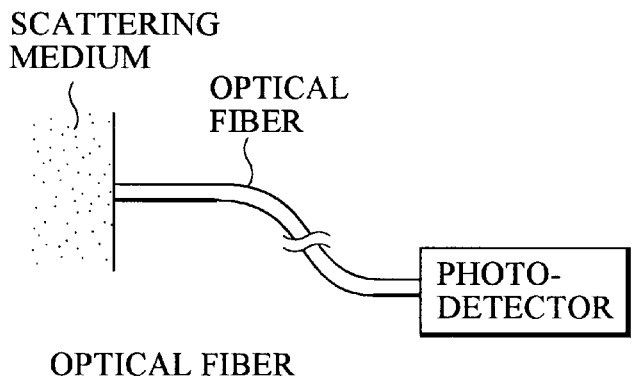
Figure 10C:
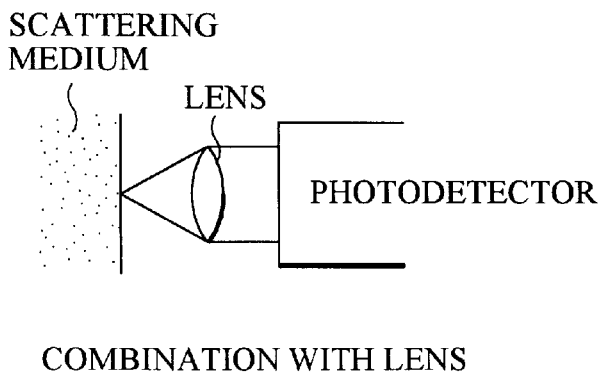

The means for detecting the light having diffuse-propagated inside the scattering medium 2 may be either one of a method for direct detection (FIG. 10A), a method using an optical fiber (FIG. 10B), a method using a lens (FIG. 10C), and so on, in addition to the method using the light guide 13 shown in FIG. 5.

Embodiment 2

While the relative positional relation is kept constant (fixed) between the light incidence position P and the photodetection position Q of the pulsed light in the above first embodiment, measurements can be carried out by scan along the scattering medium 2 and using a concentration of the absorptive constituent at an arbitrary position as a reference value, thereby measuring a spatial distribution of difference in the concentration from the reference value. In this case, similarly as in first embodiment, the spatial distribution of difference in the concentration of absorptive constituent from the reference value can be measured by use of Eqs. (8) to (11).

Figure 11:
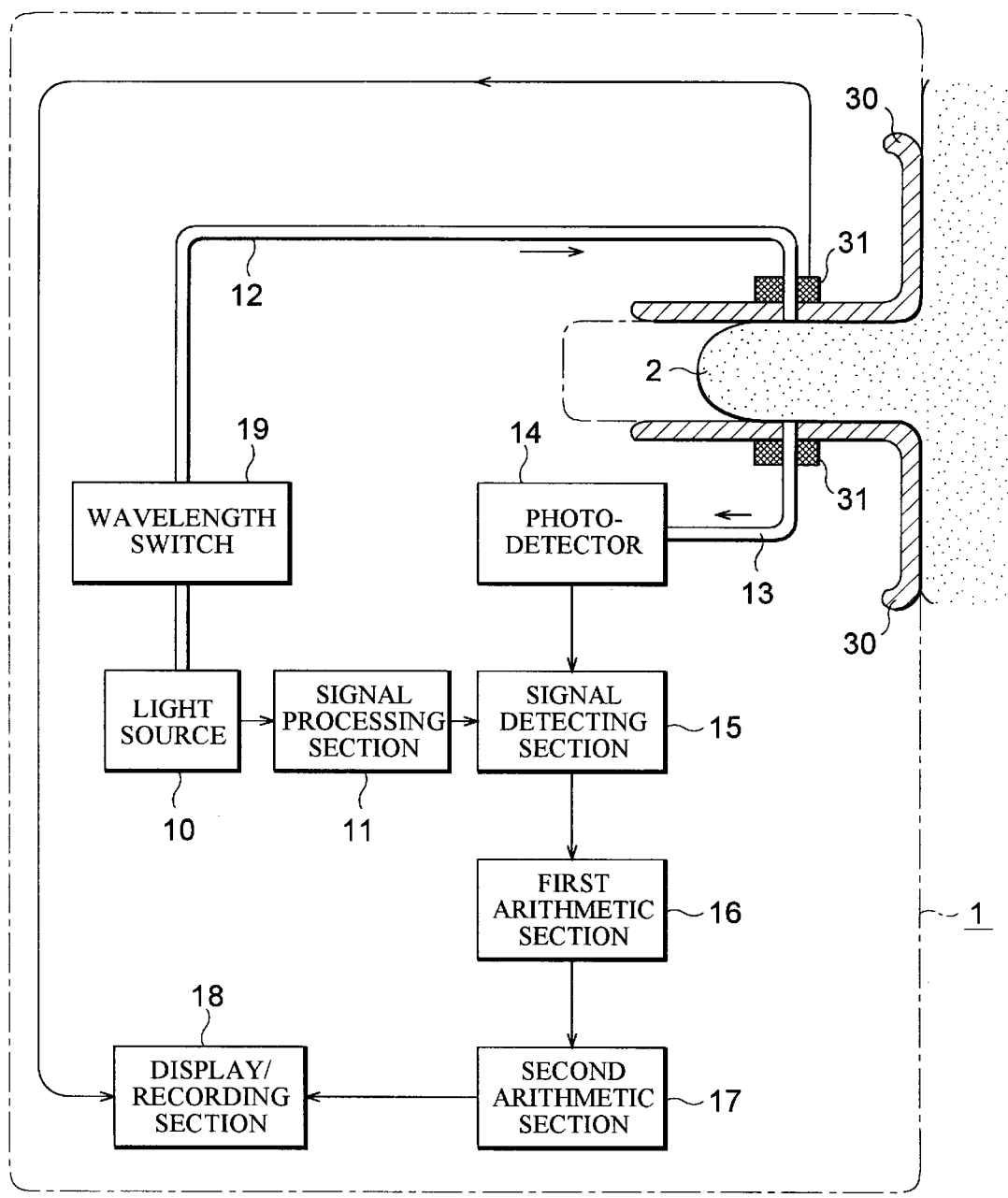
FIG. 11 is a schematic diagram to show the configuration of the apparatus in the second embodiment according to the present invention.

FIG. 11 shows the second embodiment of the apparatus of the present invention for carrying out the method of the present invention and illustrates the configuration of apparatus 1 for measuring the spatial distribution of concentration of absorptive constituent inside the scattering medium 2 like the breast lightly nipped so as to have parallel and flat surfaces. In FIG. 11 the same reference symbols are used for the elements having the same functions as those shown in FIG. 5 associated with the foregoing first embodiment. The pulsed light of predetermined wavelength $\lambda$ is incident to the surface of scattering medium 2 and the light having propagated inside the scattering medium 2 is received at a position in the surface on the opposite side. On this occasion, measurements are carried out while moving the light incidence position and photodetection position of the pulsed light with keeping the relative positional relation between them constant. Then, the spatial distribution of concentration difference of absorptive constituent can be measured, for example, by using a concentration of the absorptive constituent upon a measurement at the first measuring position (the first light incidence position and first photodetection position), as a reference value (i.e., a reference value for measurement of change amount).

This second embodiment is provided with first mechanical section 30 for lightly nipping the scattering medium 2 in parallel. Namely, the scattering medium 2 like the breast is measured in a slightly flattened state. This first mechanical section 30 is equipped with second mechanical section 31 for carrying out measurements while synchronously moving the light incidence position (incidence section) and photodetection position (light receiving section) of the pulsed light along the scattering medium with keeping the relative positional relation constant between the light incidence position and the photodetection position of the pulsed light. Then this second mechanical section 31 generates a position signal indicating a scanning position and this position signal is supplied to the display/recording section 18 to be used for calculation and display/recording of spatial distribution. Further, wavelength selector 19 is provided in the post-stage of the light source 10 for generating the pulsed light, thereby permitting selection of pulsed light of a desired wavelength as occasion may demand. The other portions are the same as those in the apparatus of the first embodiment.

This apparatus 1 of the second embodiment is arranged to extract the initial portion of output light by the gate signal, and the spatial resolution can be enhanced by narrowing the gate time on that occasion. Although the above arrangement used the pulsed light of one wavelength, pulsed light of two or more wavelengths may be applied in practice. Further, it is also possible to make the light incident at one light incidence position and to detect the propagating light at two or more photodetection positions simultaneously or in time division.

Embodiment 3

Figure 12:
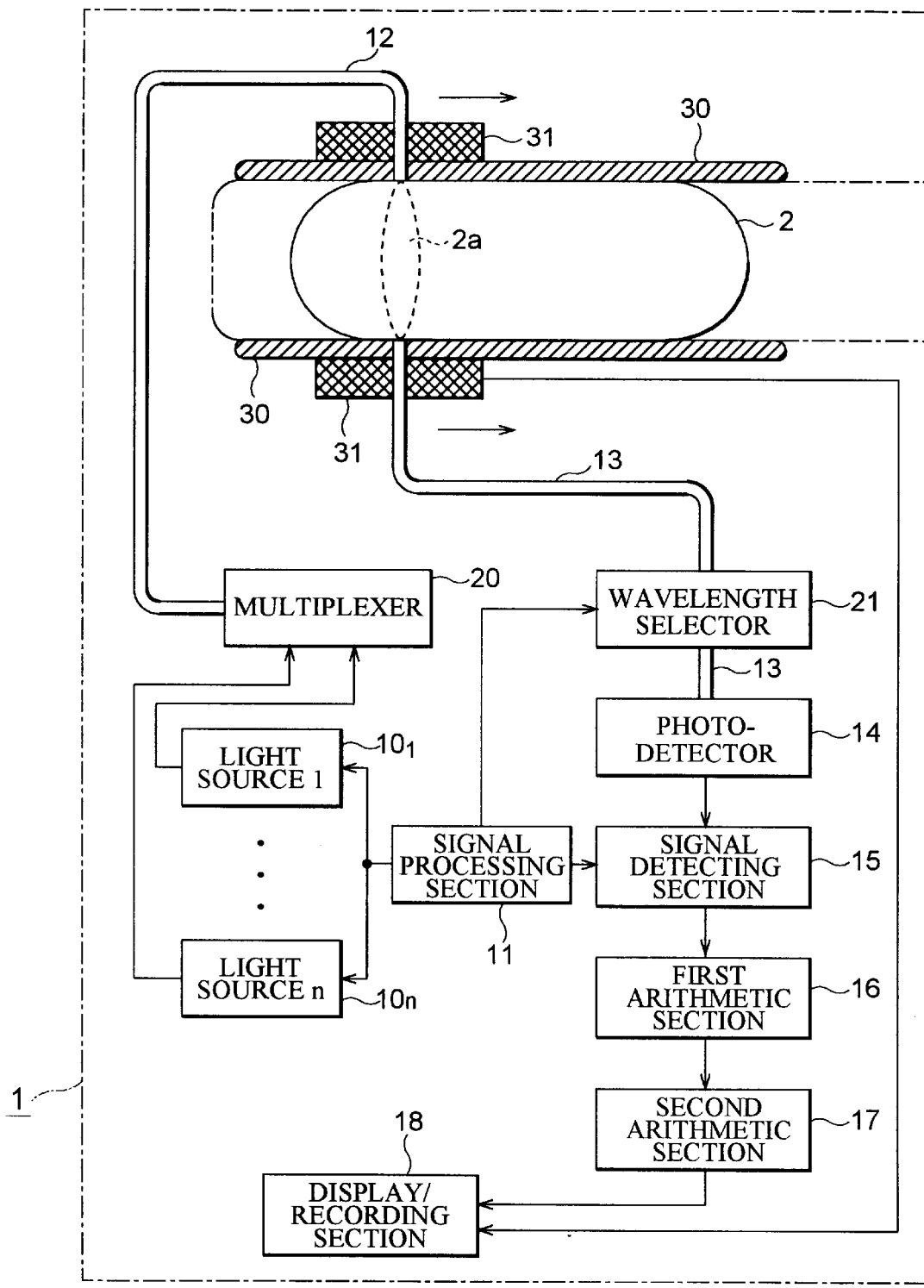
FIG. 12 is a schematic diagram to show the configuration of the apparatus in the third embodiment according to the present invention.

FIG. 12 shows the third embodiment of the apparatus of the present invention for carrying out the method of the present invention and illustrates the configuration of apparatus 1 for measuring a concentration distribution of absorptive constituent inside the scattering medium 2. In this case, the scattering medium 2 like the breast is nipped lightly. In FIG. 12 the same reference symbols are used for the elements having the same functions as those shown in FIG. 5 associated with the first embodiment and shown in FIG. 11 associated with the second embodiment. This configuration of apparatus 1 employs pulsed light beams of n different wavelengths $\lambda_1$ to $\lambda_n$ at which the scattering medium 2 shows scattering coefficients equal to each other or regarded as equal to each other, and can perform imaging of concentrations of (n−1) types of absorptive constituents by use of aforementioned Eq. (17). This third embodiment has the configuration very similar to the aforementioned second embodiment, but the measuring parameter is the spatial distribution of concentration of absorptive constituent. In addition, the measuring position (the light incidence position and photodetection position) is moved, but the relative positional relation between the light incidence position (light incidence point) and the photodetection position (light receiving point) of the pulsed light may change, because a concentration of the absorptive constituent at each scan position is measured based on foregoing Eq. (17). Specifically, the second embodiment described above was arranged to pinch the scattering medium 2 in parallel and to scan it with keeping the relative positional relation constant between the light incidence position and the photodetection position, whereas the third embodiment has no such limitation. The reason is as described in the foregoing section of (measurement of spatial distribution of concentration of absorptive constituent).

Light sources $10_1$ to $10_n$ are laser diodes, which successively generate pulsed light beams of n different wavelengths. On this occasion, oscillation timings of light sources $10_1$ to $10_n$ are controlled by a signal from signal processing section 11. The pulsed light beams from the light sources $10_1$ to $10_n$ are multiplexed in multiplexer 20 and the multiplexed light is made incident trough light guide 12 to the surface of scattering medium 2 being a measured object.

The space between the light guide 12 and the scattering medium 2 is very small in the embodiment of FIG. 12. However, in practice, this space may be expanded and may be filled with the interface material having the refractive index and scattering coefficient nearly equal to those of the scattering medium 2, as in the first embodiment. It poses no problem at all, because the pulsed light propagates in this interface material to enter the measured object. When reflection on the surface of scattering medium 2 is problematic, influence of the surface reflection or the like can be reduced by properly selecting the interface material.

The light having propagated inside the scattering medium 2 is received by light guide 13 placed at the position on the opposite side to the light incidence position. The interface material may be used herein for the same reason as above. A light signal from the light guide 13 is subjected to wavelength selection by wavelength selector 21 and the light signal corresponding to the incident pulsed light beam of each wavelength is guided through the light guide 13 to next-stage photodetector 14.

The scattering medium 2 is nipped lightly by the first mechanical section 30 as in the second embodiment. This first mechanical section 30 is provided with second mechanical section 31 for synchronously moving the light incidence position and photodetection position of the pulsed light. This second mechanical section 31 generates a position signal indicating a scanning position and this position signal is supplied to the display/recording section 18 to be used for calculation of spatial distribution and display/recording of result thereof.

The photodetector 14 converts the light signal of each wavelength described above to an electric signal, amplifies it if necessary, and outputs a detection signal. The photodetector 14 may be selected from the phototube, photodiode, avalanche photodiode, PIN photodiode, streak camera, streak scope, photo-oscilloscope, and so on, in addition to the photomultiplier tube. In selection of the photodetector 14, it is expected to have the spectral sensitivity characteristics for detecting the light of predetermined wavelengths and the necessary temporal response speed. For weak light signals, a high-gain photodetector is used. Further, the time correlation photon counting method for counting photons may be applied. The other places than the light receiving surface of photodetector 14 are desirably constructed in the structure for absorbing or intercepting the light.

Signal detecting section 15 cuts a predetermined time zone out of the aforementioned detection signal to output a measurement signal. A gate signal for cutting out the predetermined time zone is generated in signal processing section 11. The spatial resolution can be controlled by arranging the time width (gate time) of the gate signal variable and the spatial resolution is enhanced by narrowing the gate time. For example, when a fore portion of the detection signal is extracted by a narrow gate, the light having propagated in a narrow portion 2a inside the scattering medium will be measured. With increasing gate time the light having propagated in a wider portion than the portion 2a will be measured, which lowers the spatial resolution. The above acquisition of measurement signal may be done by another method, for example, by a method of direct gating by the photodetector, as shown in FIG. 7 and FIG. 8 described previously.

First arithmetic section 16 calculates the time integration value $I_T$ and mean optical pathlength $L_T$ (equivalent to the barycenter of waveform (mean time delay)) from the measurement signal. On this occasion, the mean optical pathlength $L_T$ is calculated according to aforementioned Eq. (5). Second arithmetic section 17 calculates concentrations of the (n−1) types of absorptive constituents contained in the portion 2a inside the scattering medium 2 by use of the n time integration values $I_{T1}$ to $I_{Tn}$, n mean optical pathlengths $L_{T1}$ to $L_{Tn}$, obtained in the above measurement, and n extinction coefficients. These arithmetic processes are carried out at high speed by microcomputers or the like incorporated in the first and second arithmetic sections.

Then the above sequential measurement is repeated with changing the measuring position by the second mechanical section 31, thereby calculating concentrations of the absorptive constituents at each measuring position (the light incidence position and photodetection position). The display/recording section 18 has a function to store concentrations of the absorptive constituents obtained as described above and displays or records these.

The above case was described with the method for making the pulsed light beams of the n wavelengths successively incident, but it is also possible to employ a method for simultaneously turning the pulsed light beams of n wavelengths on and making them incident coaxially. In this case there are also applicable methods including a method for selecting the wavelength by wavelength selector 21 provided immediately before the photodetector 14 and a method for splitting the detected light into n, effecting wavelength selection thereon, and thereafter detecting them by n photodetectors in parallel.

FIG. 12 showed the nearly parallel nipping arrangement of scattering medium 2, but the thickness thereof may differ in practice, as described previously. In this case, however, the second mechanical section 31 is arranged to move along the surface of scattering medium 2. Further, FIG. 12 shows the upper and lower (vertical on the plane of figure) arrangement of the light incidence position and photodetection position, but image reconstruction like CT may be made including data measured with keeping these positions in an oblique positional relation.

Embodiment 4

Figure 13:
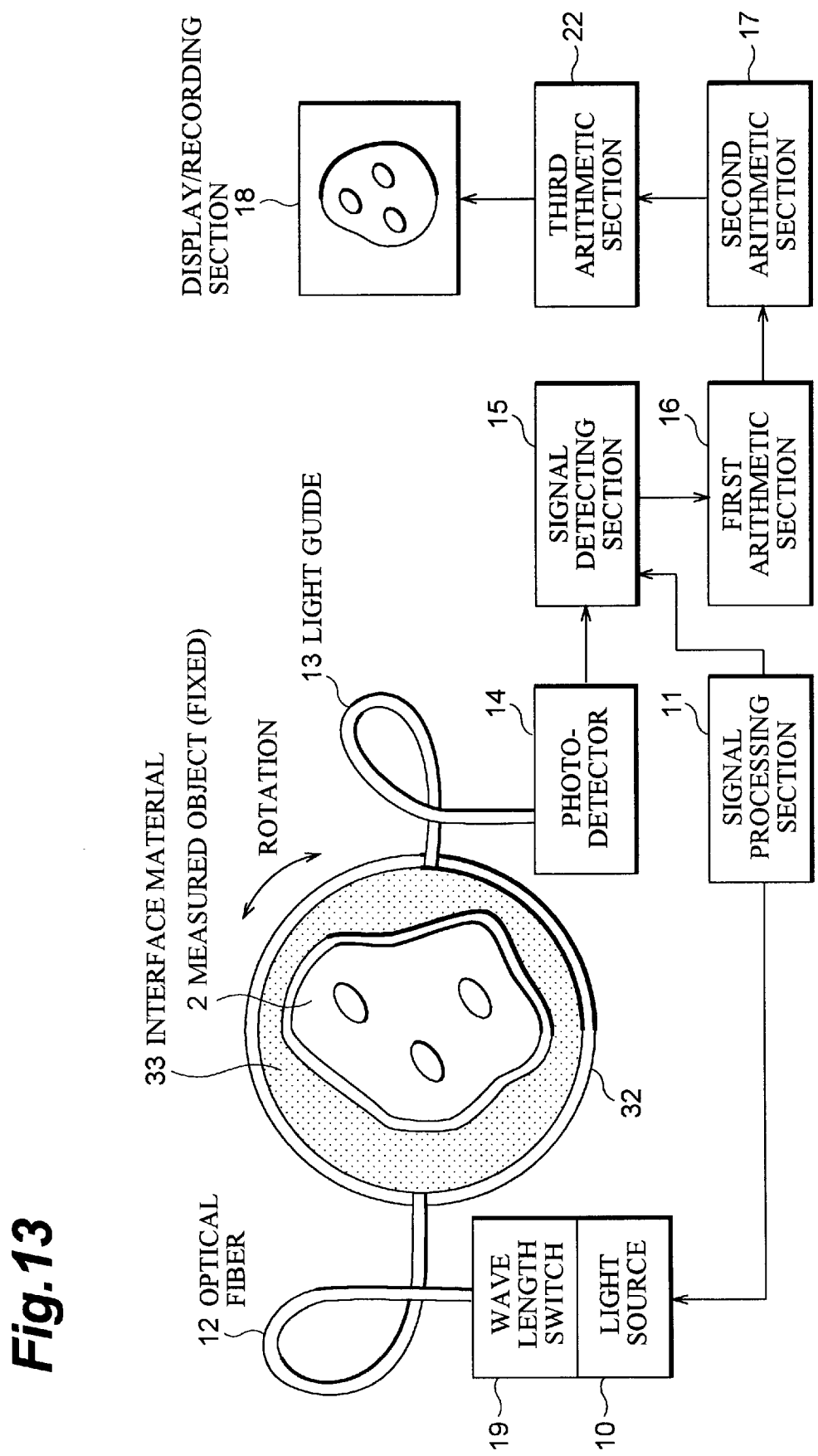
FIG. 13 is a schematic diagram to show the configuration of the apparatus in the fourth embodiment according to the present invention.

FIG. 13 shows the fourth embodiment of the apparatus of the present invention for carrying out the method of the present invention and illustrates the configuration of apparatus for measuring a concentration distribution of absorptive constituent in a cross section of scattering medium 2. The light incidence position (light incidence section) and the photodetection position (light receiving section) are moved along a periphery of scattering medium 2. In FIG. 13 the same reference symbols are used for the elements having the same functions as those shown in FIG. 5 associated with the first embodiment, shown in FIG. 11 associated with the second embodiment, and shown in FIG. 12 associated with the third embodiment. This configuration of apparatus uses pulsed light beams of two different wavelengths $\lambda_1$ and $\lambda_2$ at which the scattering coefficients are equal to each other or are regarded as equal to each other. Then a concentration of a specific absorptive constituent at each measuring position (the light incidence position and photodetection position) is obtained by use of aforementioned Eq. (17) and a distribution of concentration of the specific absorptive constituent in the cross section of scattering medium 2 is obtained from concentration values of the specific absorptive constituent at a plurality of measuring positions. This apparatus of the fourth embodiment has the configuration very similar in the other portions than around the light incidence position and photodetection position to the third embodiment described above, but a measurement result is obtained as a tomographic image.

The scattering medium 2 being the measured object is set in circular rotation mechanical section 32 surrounding the scattering medium 2. Interface material 33 fills the gap between the scattering medium 2 and the internal wall of rotation mechanical section 32 and the rotation mechanical section 32 is arranged to rotate while fixing the scattering medium 2. The rotation mechanical section 32 is equipped with optical fiber 12 for incidence of light and light guide 13 for reception of light. This rotation mechanical section 32 generates a position signal indicating a scanning position and this position signal is supplied to third arithmetic section 22 to be used for reconstruction of tomographic image.

The light source 10 is a laser diode or the like to generate two pulsed light beams of different wavelengths and wavelength switch 19 lets the two pulsed light beams pass alternately as switching them one from another. Oscillation of the light source 10 and switch timing of wavelength switch 19 are controlled by a signal from signal processing section 11. On this occasion, it is also permissible to employ pulsed light sources of two different wavelengths and turn them alternately on. It is also possible to employ a method for making the pulsed light beams of two wavelengths simultaneously incident. In this case, the wavelength selector 19 is omitted and a wavelength selector is provided in a preceding stage of photodetector 14 described below to select the wavelength used for measurement.

The pulsed light emitted from the wavelength switch 19 is incident through the optical fiber 12 to the surface of interface material 33 surrounding the scattering medium 2 being the measured object. The interface material 33 is the one already described in the first embodiment. The light having propagated inside the scattering medium 2 and interface material 33 is received by the light guide 13 disposed at the position on the opposite side to the light incidence position. A light signal from the light guide 13 is guided to the next-stage photodetector 14.

The photodetector 14 converts light signals of the two wavelengths to electric signals, amplifies them if necessary, and outputs detection signals. The photodetector 14 may be selected from the phototube, photodiode, avalanche photodiode, PIN photodiode, streak camera, streak scope, photo-oscilloscope, and so on, in addition to the photomultiplier tube. For weak light signals, a high-gain photodetector is used. Further, the time correlation photon counting method for counting photons may be applied. The other places than the light receiving surface of photodetector 14 are desirably constructed in the structure for absorbing or intercepting the light.

Signal detecting section 15 cuts a predetermined time zone out of the detection signal to output a measurement signal. A gate signal for cutting out the predetermined time zone is generated in the signal processing section 11. The spatial resolution can be controlled by arranging the time width (gate time) of the gate signal variable and the spatial resolution can be enhanced by narrowing the gate time. The above acquisition of measurement signal may be replaced by another method, for example, by a method for direct gating by the photodetector, as shown in FIG. 7 and FIG. 8 described above.

First arithmetic section 16 calculates the time integration value $I_T$ and mean optical pathlength $L_T$ (equivalent to the barycenter of waveform (mean time delay)) from the measurement signal. On this occasion, the mean optical pathlength is calculated according to aforementioned Eq. (5). Second arithmetic section 17 calculates the concentration of the specific absorptive constituent at the aforementioned measuring position by use of the two time integration values $I_{T1}$ and $I_{T2}$, the two mean optical pathlengths $L_{T1}$ and $L_{T2}$, obtained in the above measurement, and the two extinction coefficients.

These arithmetic processes are carried out at high speed by microcomputers or the like incorporated in the first and second arithmetic sections.

Next, the above sequential measurement is repeated with changing the measuring position (the light incidence position and photodetection position) by rotating the rotation mechanical section 32 by a suitable angle, thereby calculating concentrations of the absorptive constituent at respective measuring positions. The third arithmetic section 22 calculates a concentration distribution (tomographic image) of the absorptive constituent in the cross section from the values of concentrations of the absorptive constituent at the plural measuring positions, obtained in this way.

Display/recording section 18 has a function to store the concentration distribution of absorptive constituent obtained as described above and displays or records these as a tomographic image. Techniques or hardware well known in the field of CT can be utilized for the above reconstruction of tomographic image.

The above embodiment was arranged to keep the relative positional relation constant between the light incidence position and the photodetection position of the pulsed light, but this relative positional relation may be arranged as variable. Since this case increases the sampling density for the scattering medium and also increases the number of measurement data, the spatial resolution of tomographic image is enhanced. Further, it is also possible to realize CT for three-dimensional analysis by three-dimensionally variably controlling the relative positional relation between the light incidence position and the photodetection position of the pulsed light.

As described above, the absorption information measuring methods and apparatus of scattering medium according to the present invention can measure at high spatial resolution the concentration change or the absolute concentration of a specific absorptive constituent inside the scattering medium of an arbitrary shape comprised of non-reentrant surfaces. Accordingly, the present invention can greatly improve the measurement accuracy as to the specific absorptive constituent in a specific portion and can provide the measuring methods and apparatus of absorption information inside the scattering medium, such as the living-body measuring method and apparatus, imaging method and apparatus, fluoroscopic method and apparatus, tomographic image analyzing method and apparatus, or mammographic method and apparatus, capable of measuring the temporal change or the spatial distribution without being affected by the contours of scattering medium and at high spatial resolution.

From the invention thus described, it will be obvious that the invention may be varied in many ways. Such variations are not to be regarded as a departure from the spirit and scope of the invention, and all such modifications as would be obvious to one skilled in the art are intended for inclusion within the scope of the following claims.

The basic Japanese Application No. 263047/1996 filed on Oct. 3, 1996 is hereby incorporated by reference.

What is claimed is:

1. A method of measuring absorption information of a scattering medium, comprising:

generating a pulsed light of a predetermined wavelength;

making the pulsed light incident in a light spot at a light incidence position on a surface of a scattering medium;

receiving the pulsed light having propagated inside the scattering medium at a photodetection position on the surface of the scattering medium;

temporally cutting a portion out of a light signal received from the photodetection position at a signal detecting section to acquire a measurement signal;

repetitively performing the generating a pulsed light, the making the pulsed light incident, the receiving the pulsed light, and the temporally cutting at plural timings;

deriving plural time integration values and plural mean optical pathlengths for each measurement signal obtained at the plural timings; and calculating a change amount of absorption coefficient occurring between the plural timings, based on a predetermined relation among the plural time integration values, the plural mean optical pathlengths, and the change amount of absorption coefficient.

2. The method of claim 1, further comprising:

calculating a change amount of concentration of an absorptive constituent occurring between the plural timings based on a predetermined relation among the change amount of absorption coefficient, an absorption coefficient per unit concentration of the absorptive constituent, and the change amount of concentration of the absorptive constituent.

3. The method of claim 1, wherein said calculating a change amount of concentration of an absorptive constituent occurring between the plural timings is calculated based on a predetermined relation among the plural time integration values, the plural mean optical pathlengths, an absorption coefficient per unit concentration of the absorptive constituent, and the change amount of concentration of the absorptive constituent.

4. A method of measuring absorption information of a scattering medium, comprising:

generating a pulsed light of a predetermined wavelength;

making the pulsed light incident in a light spot at a light incidence position on a surface of a scattering medium;

receiving the pulsed light having propagated inside the scattering medium at a photodetection position on the surface of the scattering medium;

temporally cutting a portion out of a light signal received from the photodetection position at a signal detecting section to acquire a measurement signal;

repetitively performing the generating a pulsed light, the making the pulsed light incident, the receiving the pulsed light, and the temporally cutting at plural measurement positions while fixing a distance between the light incidence position and the photodetection position;

deriving a time integration value and a mean optical pathlength for each measurement signal obtained at the plural measurement positions; and calculating a difference of absorption coefficient occurring between the plural measurement positions based on a predetermined relation among the plural time integration values, the plural mean optical pathlengths, and the difference of absorption coefficient.

5. The method of claim 4, further comprising:

calculating a difference of concentration of an absorptive constituent occurring between the plural measurement positions based on a predetermined relation among the difference of absorption coefficient, an absorption coefficient per unit concentration of the absorptive constituent, and the difference of concentration of the absorptive constituent.

6. The method of claim 4, wherein said calculating a difference of concentration of an absorptive constituent occurring between the plural measurement positions is calculated based on a predetermined relation among the plural time integration values, the plural mean optical pathlengths, an absorption coefficient per unit concentration of the absorptive constituent, and the difference of concentration of the absorptive constituent.

7. A method of measuring absorption information of a scattering medium, comprising:

generating pulsed light of different wavelengths and scattering coefficients of a scattering medium substantially are equal to each other;

making the pulsed light incident in a light spot at a light incidence position on a surface of a scattering medium;

receiving the pulsed light having propagated inside the scattering medium at a photodetection position on the surface of the scattering medium;

temporally cutting a portion out of a light signal received from the photodetection position at a signal detecting section to acquire a measurement signal so as to keep an identical temporal relation for the pulsed light of different wavelengths;

obtaining plural time integration values and plural mean optical pathlengths for each measurement signal; and calculating a difference of absorption coefficient for the pulsed light of different wavelengths based on a predetermined relation among the plural time integration values, the plural mean optical pathlengths, and the difference of absorption coefficient.

8. The method of claim 7, further comprising:

calculating a concentration of an absorptive constituent based on a predetermined relation among the difference of absorption coefficient, absorption coefficients per unit concentration of the absorptive constituent for the pulsed light of different wavelengths, and the concentration of the absorptive constituent.

9. The method of claim 8 further comprising:

moving the light incidence position and the photodetection position along a periphery of the scattering medium, thereby creating a plurality of measurement positions;

calculating the concentration of the absorptive constituent obtained from the plurality of measurement positions; and calculating a tomographic image of a concentration distribution in the scattering medium based on the calculating of the concentration of the absorptive constituent.

10. The method of claim 7, wherein said calculating a concentration of an absorptive constituent is calculated based on a predetermined relation among the plural time integration values, the plural mean optical pathlengths, the absorption coefficients per unit concentration of the absorptive constituent for the pulsed light of different wavelengths, and the concentration of the absorptive constituent.

11. The method of claim 10, wherein said receiving the pulsed light is received at a plurality of photodetection positions, wherein said acquiring the measurement signals are acquired respectively corresponding to the pulsed light of different wavelengths at each of the plurality of photodetection positions, wherein said obtaining the plural time integration values and the plural mean optical pathlengths for each of the plural measurement signals, and wherein said calculating the concentration of the absorptive constituent is calculated based on a predetermined relation among the plural time integration values, the plural mean optical pathlengths, the absorption coefficients per unit concentration of the absorptive constituent for the pulsed light of different wavelengths, and the concentration of the absorptive constituent.

12. An apparatus for measuring absorption information of a scattering medium, comprising:

a light source to generate pulsed light having a predetermined wavelength;

a light incidence section to make the pulsed light incident at a light incidence position on surface of the scattering medium;

a light receiving section to receive the pulsed light having propagated inside the scattering medium at a photodetection position;

a signal detecting section to receive the pulsed light from the photodetection position and to temporally cut a portion out of a light signal obtained in said light receiving section to acquire a measurement signal;

a first arithmetic section to calculate the measurement signal at plural timings and derives plural time integration values and plural mean optical pathlengths for each measurement signal obtained at the plural timings; and a second arithmetic section to calculate the change amount of absorption coefficient that occurs between the plural timings based on the predetermined relation among the plural time integration values, the plural mean optical pathlengths, and the change amount of absorption coefficient.

13. The apparatus of claim 12, wherein the second arithmetic section further calculates a change amount of concentration of the absorptive constituent that occurs between the plural timings based on the predetermined relation among the change amount of absorption coefficient obtained in the second arithmetic section, the absorption coefficient per unit concentration of the absorptive constituent, and the change amount of concentration of the absorptive constituent.

14. The apparatus of claim 12, wherein the second arithmetic section further calculates the change amount of concentration of the absorptive constituent that occurs between the plural timings based on the predetermined relation among the plural time integration values, the plural mean optical pathlengths, the absorption coefficient per unit concentration of the absorptive constituent, and the change amount of concentration of the absorptive constituent.

15. An apparatus for measuring absorption information of a scattering medium, comprising:

a light source to generate a pulsed light having a predetermined wavelength;

a light incidence section to receive the pulsed light incident at a light incidence position on the surface of the scattering medium;

a light receiving section to receive the pulsed light having propagated inside the at a scattering medium at a photodetection position;

a signal detecting section to receive the pulsed light from the photodetection position and to temporally cut a portion out of the light signal obtained in said light receiving section to acquire a measurement signal;

a first arithmetic section to calculate the measurement signal at plural measurement positions while fixing the distance between the light incidence position and the photodetection position, and derives plural time integration values and plural mean optical pathlengths for each measurement signal obtained at the plural measurement positions; and a second arithmetic section to calculate the change amount of absorption coefficient that occurs between the plural measurement positions based on the predetermined relation among the plural time integration values, the plural mean optical pathlengths, and the change amount of absorption coefficient.

16. The apparatus of claim 15, wherein the second arithmetic section further calculates the difference of concentration of the absorptive constituent that occurs between the plural measurement positions based on the predetermined relation among the change amount of absorption coefficient obtained in the second arithmetic section, the absorption coefficient per unit concentration of the absorptive constituent, and the difference of concentration of the absorptive constituent.

17. The apparatus of claim 15, wherein the second arithmetic section further calculates the difference of concentration of the absorptive constituent that occurs between the plural measurement positions based on the predetermined relation among the plural time integration values, the plural mean optical pathlengths, the absorption coefficient per unit concentration of the absorptive constituent, and the difference of concentration of the absorptive constituent.

18. An apparatus for measuring absorption information of a scattering medium, comprising:

a light source to generate the pulsed light of different wavelengths and the plurality of scattering coefficients of the scattering medium that substantially are equal to each other;

a light incidence section to make the pulsed light incident at a light incidence position on the surface of the scattering medium;

a light receiving section to receive the pulsed light having propagated inside the scattering medium at a photodetection position;

a signal detecting section to temporally cut a portion out of the light signal obtained in said light receiving section to acquire a measurement signal and an identical temporal relation for each pulsed light having different wavelengths;

a first arithmetic section to obtain plural time integration values and plural mean optical pathlengths for each measurement signal; and a second arithmetic section to calculate the change amount of absorption coefficient for the pulsed light of different wavelengths based on the predetermined relation among the plural time integration values, the plural mean optical pathlengths, and the change amount of absorption coefficient.

19. The apparatus of claim 18, wherein the second arithmetic section further calculates the concentration of the absorptive constituent based on the predetermined relation among the difference of absorption coefficient obtained in the second arithmetic section, the absorption coefficients per unit concentration of the absorptive constituent for the pulsed light of different wavelengths, and the concentration of the absorptive constituent.

20. The apparatus of claim 19, further comprising:

a third arithmetic section to move the light incidence position in the light incidence section and the photodetection position in the light receiving section along a periphery of the scattering medium to generate a plurality of measurement positions;

wherein the second arithmetic section calculates the concentration of the absorptive constituent of the scattering medium for each measurement position; and wherein the third arithmetic section calculates the tomographic image of the concentration distribution in the scattering medium based on the calculations of the second arithmetic section.

21. The apparatus of claim 18, wherein the second arithmetic section further calculates the concentration of the absorptive constituent based on the predetermined relation among the plural time integration values, the plural mean optical pathlengths, the absorption coefficients per unit concentration of the absorptive constituent for the pulsed light of different wavelengths, and the concentration of the absorptive constituent.

22. The apparatus of claim 21,
wherein the light receiving section receives the light at the plurality of photodetection positions;
wherein the signal detecting section acquires the plurality of measurement signals that respectively correspond to the pulsed light of different wavelengths at each of the plurality of photodetection positions;
wherein the first arithmetic section derives the time integration value and the mean optical pathlength for each of the plurality of measurement signals; and
wherein the second arithmetic section further calculates the concentration of the absorptive constituent based on the predetermined relation among the plural time integration values, the plural mean optical pathlengths, the plurality of absorption coefficients per unit concentration of the absorptive constituent for the pulsed light of different wavelengths, and the concentration of the absorptive constituent.

* * * * *